(12) United States Patent
John et al.

(10) Patent No.: US 10,449,177 B2
(45) Date of Patent: Oct. 22, 2019

(54) METHODS OF TREATING MILD COGNITIVE IMPAIRMENT (MCI) AND RELATED DISORDERS

(75) Inventors: Varghese John, San Francisco, CA (US); Dale E. Bredesen, Novato, CA (US)

(73) Assignee: Buck Institute for Research on Aging, Novato, CA (US)

( * ) Notice: Subject to any disclaimer, the term of this patent is extended or adjusted under 35 U.S.C. 154(b) by 0 days.

(21) Appl. No.: 13/213,960

(22) Filed: Aug. 19, 2011

(65) Prior Publication Data

US 2012/0071468 A1 Mar. 22, 2012

Related U.S. Application Data

(60) Provisional application No. 61/401,907, filed on Aug. 19, 2010.

(51) Int. Cl.
*A61K 31/4035* (2006.01)
*A61K 31/05* (2006.01)
*A61K 31/145* (2006.01)
*A61K 31/5513* (2006.01)

(52) U.S. Cl.
CPC .......... *A61K 31/4035* (2013.01); *A61K 31/05* (2013.01); *A61K 31/145* (2013.01); *A61K 31/5513* (2013.01)

(58) Field of Classification Search
None
See application file for complete search history.

(56) References Cited

U.S. PATENT DOCUMENTS

| | | | |
|---|---|---|---|
| 5,373,021 A | 12/1994 | Marangos | |
| 8,470,846 B2 | 6/2013 | Hashimoto et al. | |
| 2002/0052340 A1 | 5/2002 | Jerussi et al. | |
| 2002/0052341 A1 | 5/2002 | Fang et al. | |
| 2002/0107244 A1 | 8/2002 | Howard | |
| 2002/0115727 A1 | 8/2002 | Senanayake et al. | |
| 2002/0188029 A1 | 12/2002 | Jerussi et al. | |
| 2003/0195261 A1 | 10/2003 | Jerussi et al. | |
| 2004/0092511 A1 | 5/2004 | Billstein et al. | |
| 2004/0121010 A1 | 6/2004 | Hirsh et al. | |
| 2004/0122104 A1 | 6/2004 | Hirsh et al. | |
| 2004/0132826 A1 | 7/2004 | Hirsh et al. | |
| 2004/0142904 A1 | 7/2004 | Rariy et al. | |
| 2004/0224960 A1 | 11/2004 | Borchardt et al. | |
| 2006/0111450 A1* | 5/2006 | Pasinetti | 514/729 |
| 2006/0205969 A1 | 9/2006 | Xu et al. | |
| 2007/0059367 A1 | 3/2007 | Cherukuri | |
| 2007/0112017 A1 | 5/2007 | Barlow et al. | |
| 2007/0197551 A1 | 8/2007 | Sato et al. | |
| 2008/0103166 A1 | 5/2008 | Hashimoto et al. | |
| 2008/0200508 A1 | 8/2008 | Rariy et al. | |
| 2009/0048289 A1 | 2/2009 | Tremel et al. | |
| 2009/0156581 A1 | 6/2009 | Dillon et al. | |
| 2009/0163451 A1 | 6/2009 | Porreca et al. | |
| 2009/0298809 A1 | 12/2009 | Manning et al. | |
| 2010/0099701 A1 | 4/2010 | Gant et al. | |
| 2011/0003005 A1 | 1/2011 | Venkatesh et al. | |
| 2011/0092535 A1 | 4/2011 | Barnes | |
| 2011/0207830 A1 | 8/2011 | Kim et al. | |
| 2011/0244034 A1 | 10/2011 | Jain et al. | |
| 2011/0280925 A1 | 11/2011 | Tan et al. | |
| 2013/0231311 A1 | 9/2013 | Farr et al. | |
| 2013/0231315 A1 | 9/2013 | Fadini et al. | |
| 2013/0267487 A1 | 10/2013 | Seo et al. | |
| 2013/0274293 A1 | 10/2013 | Compan | |
| 2013/0310366 A1 | 11/2013 | Manning et al. | |
| 2013/0324572 A1 | 12/2013 | Hashimoto et al. | |
| 2015/0030683 A1 | 1/2015 | John et al. | |

FOREIGN PATENT DOCUMENTS

| | | |
|---|---|---|
| CN | 101444508 B | 10/2010 |
| EP | 1741430 | 1/2007 |
| EP | 2 238 978 A1 | 10/2010 |
| EP | 2 327 402 A2 | 6/2011 |
| EP | 2 508 174 A1 | 10/2012 |
| JP | 2010-510272 | 4/2010 |
| WO | WO 2005/105089 | 11/2005 |
| WO | WO2005102158 | 11/2005 |
| WO | WO2008074896 | 6/2008 |
| WO | WO 2010/036052 | 4/2010 |

(Continued)

OTHER PUBLICATIONS

Blennow et al., "CSF markers for incipient Alzheimer's disease," The Lancet: Neurology, 2003; 2(10): pp. 605-613. (Year: 2003).*
Dysken et al., "Odansetron in the Treatment of Cogntive Decline in Alzheimer Dementia," Am. J. Geriatri. Psychiatry 2002; 10(2): 211-215 (abstract only). (Year: 2002).*
PCT International Search Report and Written Opinion dated Jan. 27, 2012 issued in PCT/US2011/048472.
PCT International Preliminary Report on Patentability dated Feb. 19, 2013 issued in PCT/US2011/048472.
Hashimoto et al. (2006) "Phencyclidine-induced cognitive deficits in mice are improved by subsequent subchronic administration of tropisetron: role of alpha7 nicotinic receptors." *European Journal of Pharmacology* 553(1-3): 191-195.
Macor et al. (2001). "The 5-HT3 antagonist tropisetron (ICS 205-930) is a potent and selective alpha7 nicotinic receptor partial agonist". *Bioorg. Med. Chem. Lett.* 11 (3): 319-321.

(Continued)

*Primary Examiner* — Sreenivasan Padmanabhan
*Assistant Examiner* — Jody L Karol
(74) *Attorney, Agent, or Firm* — Harness Dickey & Pierce P.L.C.

(57) ABSTRACT

The invention provides compositions and methods for the treatment of mild cognitive impairment (MCI), and for inhibiting, reducing, delaying and/or preventing the progression of MCI to Alzheimer's disease. The methods entail administering an effective amount of one or more compounds selected from the group consisting of tropisetron, disulfuram, honokiol and nimetazepam. The methods also are useful for prophylactic and therapeutic treatment of amyloidogenic diseases, including Alzheimer's disease.

24 Claims, 8 Drawing Sheets

(56) References Cited

FOREIGN PATENT DOCUMENTS

WO   WO2012024616   2/2012
WO   WO 2013/123426   8/2013

OTHER PUBLICATIONS

Nie et al. (2010) "Activation of α7 nicotinic receptor affects APP processing by regulating secretase activity in SH-EP1-α7 nAChR-hAPP695 cells." *Brain Research* 1356: 112-120; One Page—Abstract Only.
Papke et al. (2005) "Molecular dissection of tropisetron, an alpha7 nicotinic acetylcholine receptor-selective partial agonist." *Neurosci. Letts.* 378: 140-144.
Pitsikas et al. (1997) "Different Effects of Tropisetron and Ondansetron in Learning and Memory Paradigms" *Pharmacology Biochemistry and Behavior* 56(4): 571-576.
Shiina et al. (2010) "A randomised, double-blind, placebo-controlled trial of tropisetron in patients with schizophrenia." *Annl. Gen. Psychiatry* 9: 27 (pp. 1-10).
EP Extended European Search Report dated Dec. 11, 2013 issued in EP11818848.1.
Callahan et al. (2003) "Characterization of nicotinic alpha7 receptor agonists in animal models of cognition." *Neuroscience Meeting Planner*. New Orleans, LA: *Society for Neuroscience*, 2003. *Abstract*—Presentation No. 625.8 One page.
Chugh et al. (1991) "Enhancement of Memory Retrieval and Attenuation of Scopolamine-Induced Amnesia Following Administration of 5-HT$_3$ Antagonist ICS 205-930" *Pharmacology & Toxicology* 69: 105-106.
Australian Patent Examination Report No. 1 dated Nov. 28, 2014 issued in Australian Patent Application No. 2011291506.
PCT International Search Report and Written Opinion dated Jun. 3, 2013 issued in PCT/US2013/026487.
PCT International Preliminary Report dated Aug. 28, 2014 issued in PCT/US2013/026487.
Ep Extended European Search Report dated Jul. 27, 2015 issued in EP 13 749 359.9.
European Office Action dated Nov. 27, 2015 issued in EP11 818 848.1.
Japanese Notice of Reasons for Rejection dated Jul. 6, 2015 issued in JP 2013-525003.
Mexican Second Office Action dated Aug. 4, 2015 issued in Mexican Patent Application MX/a/2013/001917.
U.S. Office Action dated Feb. 16, 2016 issued in U.S. Appl. No. 14/378,950.
U.S. Final Office Action dated Oct. 17, 2016 issued in U.S. Appl. No. 14/378,950.
European Reply to Communication of Nov. 27, 2015 dated Jun. 7, 2016 issued in EP 11 818 848.1.
Japanese Decision of Rejection dated Apr. 18, 2016 issued in JP 2013-525003.
Japanese Notification of Commencement of Pre-Appeal Examination dated Sep. 12, 2016 issued in JP 2013-525003.
Mexican Office Action dated Mar. 30, 2015 issued in Mexican Patent Application MX/a/2013/001917.
Mexican Third Office Action [English Description] dated Apr. 15, 2016 issued in Mexican Patent Application MX/a/2013/001917.
Mexican Fourth Office Action [English Description] dated Jan. 12, 2017 issued in Mexican Patent Application MX/a/2013/001917.
European Office Action dated Aug. 22, 2016 issued in EP 13 749 359.9.
Nie et al. (2010) "Activation of α7 nicotinic receptor affects APP processing by regulating secretase activity in SH-EP1-α7 nAChR-hAPP695 cells," *Brain Research* 1356:112-120.
Canadian Office Action dated Jun. 23, 2017 issued in CA 2,808,630.
European Office Action dated May 4, 2017 issued in EP 11 818 848.1.
Japanese Decision of Rejection dated Jun. 19, 2017 issued in JP 2013-525003.

\* cited by examiner

A

B

METHODS OF TREATING MILD COGNITIVE IMPAIRMENT (MCI) AND RELATED DISORDERS

CROSS-REFERENCE TO RELATED APPLICATIONS

This application claims priority to and benefit of U.S. Provisional Application No. 61/401,907, filed on Aug. 19, 2010, which is hereby incorporated herein by reference in its entirety for all purposes.

STATEMENT OF GOVERNMENTAL SUPPORT

This invention was made with government support under Grant No: AG034427 awarded by the National Institutes of Health. The government has certain rights in this invention.

BACKGROUND OF THE INVENTION

Alzheimer's disease (AD) is a progressive neurodegenerative disorder that is characterized by rapid cognitive and functional decline in patients diagnosed with the disease. In the early stages of the disease the patients generally suffer from mild cognitive impairment (MCI) that can convert over time to full blown AD. The disease broadly falls into two categories: a) late onset AD, that occurs generally in subjects 65 years or older and that is often correlated to numerous risk factors including presence of an APOE ε4 allele; and b) early onset AD, develops early on in subjects between 30 and 60 years of age and is generally associated with familial Alzheimer's disease (FAD) mutations in the amyloid precursor protein (APP) gene or in the presenilin gene. In both types of disease, the pathology is the same but the abnormalities tend to be more severe and widespread in cases beginning at an earlier age.

AD is generally characterized by at least two types of lesions in the brain, senile plaques composed of the Aβ peptide (and other components, typically at lower concentrations than the Aβ peptide) and neurofibrillary tangles composed primarily of intracellular deposits of microtubule associated tau protein (especially hyperphosphorylated tau). Measurement of the levels of Aβ peptide and Tau/phosphorylated Tau in cerebrospinal fluid (CSF) along with imaging analysis and cognitive/functional tests can be used clinically to determine progression of the disease and conversion to full-blown AD.

Alzheimer's disease (AD) has been viewed largely as a disease of toxicity, mediated by the collection of a small peptide (the Aβ peptide) that damages brain cells by physical and chemical properties, such as the binding of damaging metals, reactive oxygen species production, and direct damage to cell membranes. While such effects of Aβ have been clearly demonstrated, they do not offer a physiological role for the peptide.

In this regard it is noted that in therapies that showed marked reduction of β-amyloid levels in AD, limited to no cognitive improvement was observed. This was unexpected by much of the research community, as AD has been largely viewed as a disease of chemical and physical toxicity of β-amyloid (e.g., generation of reactive oxygen species, metal binding, etc.).

Recent research using transgenic mice have demonstrated that blockage of the C-terminal cleavage of amyloid precursor protein ("APP") at aspartic acid residue (D664 of $APP_{695}$) intracellularly leads to abrogation of the characteristic pathophysiological abnormalities and behavioral symptoms associated with Alzheimer's disease. The methods described herein are based, in part, on the identification of molecules that modulate the processing of APP from the pro-AD fragments (e.g., sAPPβ, Aβ, Jcasp and C-31 (Jcasp and C-31 fragment levels can be determined by measuring the levels of APPneo—a full length fragment of APP without the C-terminal 31 amino acids)) to the anti-AD fragments (e.g., sAPPα, p3 and AICD).

SUMMARY OF THE INVENTION

In certain embodiments, a method is provided of mitigating in a mammal one or more symptoms associated with mild cognitive impairment (MCI) (e.g., MCI associated with amyloid deposits in the brain). In various embodiments, the methods entail comprising administering, or causing to be administered, to the mammal one or more compounds selected from the group consisting of tropisetron, disulfuram, honokiol and nimetazepam, or a pharmaceutically acceptable salt (or other pharmaceutically acceptable form) thereof, or an analogue thereof or its pharmaceutically acceptable salt (or other pharmaceutically acceptable form), in an amount sufficient to mitigate a symptom of said MCI. In certain embodiments of these methods the compounds are administered in a therapeutically effective or prophylactically effective amount or regime. In a related aspect, the invention provides a compound selected from the group consisting of tropisetron, disulfuram, honokiol and nimetazepam, or a pharmaceutically acceptable salt (or other pharmaceutically acceptable form) thereof, or an analogue thereof or its pharmaceutically acceptable salt (or other pharmaceutically acceptable form), for use in a method of mitigating a symptom of mild cognitive impairment (MCI) associated with amyloid deposits in the brain. In certain embodiments the mammal is a human while in other embodiments, the mammal is a non-human mammal. In various embodiments the mammal is at risk of developing Alzheimer's disease. In certain embodiments the mammal has a familial risk for having Alzheimer's disease. In certain embodiments the mammal has a familial Alzheimer's disease (FAD) mutation. In certain embodiments the mammal has the APOE ε4 allele. In certain embodiments administration of the compound(s) delays or prevents the progression of MCI to Alzheimer's disease. In certain embodiments the mammal is free of and does not have genetic risk factors of Parkinson's disease or schizophrenia and/or is not diagnosed as having or at risk for Parkinson's disease or schizophrenia. In certain embodiments the mammal does not have a neurological disease or disorder other than Alzheimer's disease. In various embodiments the mitigation comprises a reduction in the CSF of levels of one or more components selected from the group consisting of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio, and/or the mitigation comprises a reduction of the plaque load in the brain of the mammal, and/or the mitigation comprises a reduction in the rate of plaque formation in the brain of the mammal, and/or the mitigation comprises an improvement in the cognitive abilities of the mammal, and/or the mitigation comprises an improvement in, and/or a stabilization of, and/or a reduction in the rate of decline of the clinical dementia rating (CDR) of the mammal, and/or the mammal is a human and the mitigation comprises a perceived improvement in quality of life by the human. In various embodiments the compound(s) can be administered in any modality that permits the compound(s) to reach the brain (e.g., to cross or to by-pass the blood brain barrier). In certain embodiments the compound is administered orally. In some embodiments, the administering is over a period of at least 3 weeks, for example, over a period of at least 4, 5, 6, 7, 8, 9, 10, 11, 12 weeks, or longer, as appropriate. In some embodiments, the administering is over a period of at least 1, 2, 3, 4, 5, 6, 7, 8, 9, 10, 11, 12 months, or longer, as appropriate. In some embodiments, the administering is for the remainder of the life of the subject. In certain embodiments, the administering comprises administering once, twice, three times, or four times daily over the treatment period. In certain embodiments the compound(s) or analog(s) thereof are formulated for administration via a route selected from the group consisting of isophoretic delivery, transdermal delivery, aerosol administration, administration via inhalation, oral administration, intravenous administration, and rectal administration. In certain embodiments the compound(s) or analog(s) thereof are administered via a route selected from the group consisting of isophoretic delivery, transdermal delivery (e.g., via a transdermal patch), aerosol administration, administration via inhalation, oral administration, intravenous administration, and rectal administration. In certain embodiments the compound(s) an acetylcholinesterase inhibitor (e.g., tacrine, ipidacrine, galantamine, donepezil, icopezil, zanapezil, rivastigmine, huperzine A, phenserine, physostigmine, neostigmine, pyridostigmine, ambenonium, demarcarium, edrophonium, ladostigil, ungeremine, and the like) is not administered in conjunction with said compound. In certain embodiments tropisetron, disulfuram, honokiol and nimetazepam, or a pharmaceutically acceptable salt (or other pharmaceutically acceptable form) thereof, or an analogue thereof or its pharmaceutically acceptable salt (or other pharmaceutically acceptable form) are the sole agents administered to the subject having a neurophysiological effect. In certain embodiments these compounds are the sole active agent(s) prescribed to the subject for mitigation of a symptom of MCI or for inhibiting or stopping the progression of MCI to AD.

Methods are also provided for lessening the severity or slowing the progression of a disease characterized by amyloid deposits in the brain in a mammal. These "therapeutic" methods involve administering, or causing to be administered, to the mammal an effective amount or effective regime of one or more compounds selected from the group consisting of tropisetron, disulfuram, honokiol and nimetazepam, or its pharmaceutically acceptable salt (or other pharmaceutically acceptable form), or an analog thereof or its pharmaceutically acceptable salt (or other pharmaceutically acceptable form), thereby reducing the risk, lessening the severity, or delaying the progression or onset of the disease. Methods are also provided for reducing the risk or delaying the onset of a disease (or reducing the ultimate severity of a disease) characterized by amyloid deposits in the brain in a mammal. These "prophylactic" methods involve administering, or causing to be administered, to the mammal an effective amount or regime of one or more compounds selected from the group consisting of tropisetron, disulfuram, honokiol and nimetazepam, or its pharmaceutically acceptable salt, or an analog thereof or its pharmaceutically acceptable salt, thereby reducing the risk, lessening the severity, or delaying the progression or onset of the disease. Similarly, in certain embodiments, these compounds (e.g., tropisetron, disulfuram, honokiol and nimetazepam, etc.) are provided for use in a method of lessening the severity or delaying the progression of a disease characterized by amyloid deposits in the brain in a mammal (e.g., a therapeutic use), and/or for use in a method of reducing the risk or delaying the onset of a disease characterized by amyloid deposits in the brain in a mammal (e.g., a prophylactic use) are provided. In certain embodiments the compound is tropisetron and/or a pharmaceutically acceptable salt (or other pharmaceutically acceptable form) thereof, or disulfuram or a pharmaceutically acceptable salt thereof, and/or honokiol or a pharmaceutically acceptable salt (or other pharmaceutically acceptable form) thereof, and/or nimetazepam or a pharmaceutically acceptable salt (or other pharmaceutically acceptable form) thereof. In certain embodiments the mammal is human or a non-human mammal. In certain embodiments the disease is mild cognitive impairment (MCI) and/or the mammal is diagnosed as having mild cognitive impairment (MCI). In certain embodiments the administration of the compound(s) delays or prevents the progression of MCI to Alzheimer's disease. In certain embodiments the disease is Alzheimer's disease (e.g., early stage AD, mid-stage AD, late stage AD). In certain embodiments the mammal is diagnosed as having Alzheimer's disease. In certain embodiments the mammal is at risk of developing Alzheimer's disease. In certain embodiments the mammal has a familial risk for having Alzheimer's disease. In certain embodiments the mammal has a familial Alzheimer's disease (FAD) mutation. In certain embodiments mammal has the APOE ε4 allele. In certain embodiments the administration of the compound(s) delays or prevents the progression of early stage AD to mid stage AD, delays or prevents the progression of mid-stage AD to late stage AD. In certain embodiments the mammal is free of and does not have genetic risk factors of Parkinson's disease or schizophrenia. In certain embodiments the mammal is not diagnosed as having or at risk for Parkinson's disease or schizophrenia. In certain embodiments the mammal does not have and/or is not diagnosed as having or as at risk for a neurological disease or disorder other than Alzheimer's disease. In certain embodiments the reduction of risk, lessening of severity, or delaying the progression or onset of the disease comprises a reduction in the CSF of levels of one or more components selected from the group consisting of Tau, phospho-Tau (pTau), APPneo, soluble Aβ40 and soluble Aβ 42, and/or comprises a reduction of the plaque load in the brain of the mammal, and/or comprises a reduction in the rate of plaque formation in the brain of the mammal, and/or comprises an improvement in the cognitive abilities of the mammal, and/or the an improvement in, and/or a stabilization of, and/or a reduction in the rate of decline of the clinical dementia rating (CDR) of the mammal, and/or comprises a perceived improvement in quality of life by the human. In certain embodiments the mammal is a human and progression from an asymptomatic state to a symptomatic state is prevented or delayed. In various embodiments the compound(s) can be administered in any modality that permits the compound(s) to reach the brain (e.g., to cross or to by-pass the blood brain barrier). In certain embodiments the compound is administered orally. In some embodiments, the administering is over a period of at least 3 weeks, for example, over a period of at least 4, 5, 6, 7, 8, 9, 10, 11, 12 weeks, or longer, as appropriate. In some embodiments, the administering is over a period of at least 1, 2, 3, 4, 5, 6, 7, 8, 9, 10, 11, 12 months, or longer, as appropriate. In some embodiments, the administering is for the remainder of the life of the subject. In certain embodiments, the administering comprises administering once, twice, three times, or four times daily over the treatment period. In certain embodiments the compound(s) or analog(s) thereof are formulated for administration via a route selected from the group consisting of isophoretic delivery, transdermal delivery, aerosol administration, administration via inhalation, oral administration, intravenous administration, and rectal administration. In certain embodiments the compound(s) or analog(s) thereof are administered via a route selected from the group consisting of isophoretic delivery, transdermal delivery (e.g., via a transdermal patch), aerosol administration, administration via inhalation, oral administration, intravenous administration, and rectal administration. In certain embodiments an acetylcholinesterase inhibitor (e.g., tacrine, ipidacrine, galantamine, donepezil, icopezil, zanapezil, rivastigmine, huperzine A, phenserine, physostigmine, neostigmine, pyridostigmine, ambenonium, demarcarium, edrophonium, ladostigil, ungeremine, and the like) is not administered in conjunction with said compound. In certain embodiments tropisetron, disulfuram, honokiol and nimetazepam, or a pharmaceutically acceptable salt (or other pharmaceutically acceptable form) thereof, or an analogue thereof or its pharmaceutically acceptable salt (or other pharmaceutically acceptable form) are the sole agents administered to the subject having a neurophysiological effect. In certain embodiments these compounds are the sole active agent(s) prescribed to the subject for therapy or prophylaxis of an amyloidogenic pathology (e.g., AD).

In a related aspect, the invention provides a compound selected from the group consisting of tropisetron, disulfuram, honokiol and nimetazepam, or a pharmaceutically acceptable salt (or other pharmaceutically acceptable form) thereof, or an analogue thereof or its pharmaceutically acceptable salt (or other pharmaceutically acceptable form), for use in a method of mitigating a symptom of mild cognitive impairment (MCI) associated with amyloid deposits in the brain.

In another aspect, the invention provides methods of preventing or treating a disease characterized by amyloid deposits or an increase in Aβ peptide concentration in an individual in need thereof. Such methods entail administering, or causing to be administered, an effective dosage of a compound (e.g., tropisetron, disulfuram, honokiol, and/or nimetazepam, or pharmaceutically acceptable salts thereof) or its pharmaceutically acceptable salt, or an analog of the compound or its pharmaceutically acceptable salt to the individual. Such methods are particularly useful for preventing or treating Alzheimer's disease in which case the amyloid deposit can comprise Aβ. The methods can be used on both asymptomatic subjects (e.g., patients) and those currently showing symptoms of disease.

In a further aspect, the invention provides methods of promoting the processing of amyloid precursor protein (APP) by the non-amyloidogenic (e.g., "anti-AD") and reducing or inhibiting processing of APP by the amyloidogenic (e.g., "pro-AD") pathway. In some embodiments, the methods comprise contacting a cell expressing APP (or causing said cell to be contacted) with a compound (e.g., tropisetron, disulfuram, honokiol and/or nimetazepam, or pharmaceutically acceptable salts thereof), or an analog of the compound or its pharmaceutically acceptable salt, in an amount sufficient to increase the processing of APP by the non-amyloidogenic pathway. In some embodiments, the cell is contacted in vivo. In some embodiments the APP isoform is APP695, the predominant isoform of APP in the brain.

In some embodiments, the mammal is human.

In some embodiments, the disease is mild cognitive impairment (MCI). In some embodiments, the mammal is diagnosed as having mild cognitive impairment (MCI). In some embodiments, the administration of tropisetron delays or prevents the progression of MCI to Alzheimer's disease.

In some embodiments, the disease is Alzheimer's disease. For example, the mammal may be diagnosed as having Alzheimer's disease, or the mammal may be at risk of developing Alzheimer's disease. The risk of developing disease may be due to environmental, life-style or genetic factors. Illustrative risk factors include without limitation, e.g., positive Pittsburgh Compound B ("PiB")-PET scan, one or more AD-associated genetic mutations, hippocampal volume loss, or a pro-AD profile cerebrospinal fluid (elevated levels of sAPPβ, Aβ, Jcasp and C-31, and/or APPneo). The mammal may have a familial risk for having Alzheimer's disease, e.g., have a parent, grandparent or sibling with Alzheimer's disease. In some embodiments, the mammal has a familial Alzheimer's disease (FAD) mutation. In some embodiments, the mammal has the APOE ε4 allele.

In some embodiments, the mammal does not have, is not diagnosed as having, and/or is not at risk for a neurological disease or disorder other than Alzheimer's disease. For example, in some embodiments, the mammal is free of, and/or is not diagnosed as having, and/or is not at risk for, and/or does not have genetic risk factors of Parkinson's disease or schizophrenia.

In some embodiments, the mammal is asymptomatic. In such cases, the administration of the compound (e.g., tropisetron, disulfuram, honokiol and/or nimetazepam, or pharmaceutically acceptable salts thereof) can delay or prevent the progression from asymptomatic to MCI or from MCI to AD or from asymptomatic to AD. In some embodiments, the progression from an asymptomatic state to a symptomatic state is prevented or delayed. In some embodiments, the progression from a symptomatic state to a more symptomatic state (e.g., MCI to AD, mild MCI to MCI, or mild AD to more severe AD) is prevented or delayed.

In some embodiments, the mitigation, reduction of risk, lessening of severity, or delaying the progression or onset of the disease comprises a reduction in the CSF of levels of one or more components selected from the group consisting of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio. In some embodiments, the mitigation, and/or reduction of risk, and/or lessening of severity, and/or delaying the progression and/or onset of the disease comprises a reduction of the plaque load in the brain of the mammal. In some embodiments, the mitigation, reduction of risk, lessening of severity, or delaying the progression or onset of the disease comprises a reduction in the rate of plaque formation in the brain of the mammal, e.g., as determined by CT, PET, PIB-PET and/or MRI. In some embodiments, the mitigation, reduction of risk, lessening of severity, or delaying the progression or onset of the disease comprises an improvement in the cognitive abilities of the mammal. In some embodiments, the mammal is a human and lessening of severity, or delaying the progression of the disease comprises a perceived improvement in quality of life by the human.

In some embodiments, the compound (e.g., tropisetron, disulfuram, honokiol and/or nimetazepam, or pharmaceutically acceptable salts thereof) or an analog thereof is formulated for administration via a route selected from the group consisting of isophoretic delivery, transdermal delivery, aerosol administration, administration via inhalation, oral administration, intravenous administration, and rectal administration. In some embodiments, the compound or an analog thereof is administered via a route selected from the group consisting of isophoretic delivery, transdermal delivery, aerosol administration, administration via inhalation, oral administration, intravenous administration, and rectal administration. In some embodiments, the compound (e.g., tropisetron, disulfuram, honokiol and/or nimetazepam, or pharmaceutically acceptable salts thereof) is administered orally. In some embodiments, the compound (e.g., tropisetron, disulfuram, honokiol and/or nimetazepam, or pharmaceutically acceptable salts thereof) is administered transdermally, e.g., via a transdermal patch.

In some embodiments, the administering is over a period of at least 3 weeks, for example, over a period of at least 4, 5, 6, 7, 8, 9, 10, 11, 12 weeks, or longer, as appropriate. In some embodiments, the administering is over a period of at least 1, 2, 3, 4, 5, 6, 7, 8, 9, 10, 11, 12 months, or longer, as appropriate. In some embodiments, the administering is for the remainder of the life of the subject. In certain embodiments, the administering comprises administering once, twice, three times, or four times daily over the treatment period.

In some embodiments, an acetylcholinesterase inhibitor is not administered in conjunction with said compound (e.g., tropisetron, and/or disulfuram, and/or honokiol, and/or nimetazepam, or pharmaceutically acceptable salts thereof). In some embodiments, tropisetron is not administered in conjunction with an acetylcholinesterase inhibitor.

DEFINITIONS

As used herein, "administering" refers to local and systemic administration, e.g., including enteral, parenteral, pulmonary, and topical/transdermal administration. Routes of administration for compounds (e.g., tropisetron, disulfuram, honokiol and/or nimetazepam) that find use in the methods described herein include, e.g., oral (per os (P.O.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering a compound or composition to a mammal so that the compound or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administering" or "concurrent administration", when used, for example with respect to the compounds (e.g., tropisetron, disulfuram, honokiol and/or nimetazepam) and/or analogs thereof and another active agent (e.g., a cognition enhancer), refers to administration of the compound and/or analogs and the active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, preferably 30% or 40% or greater, more preferably 50% or 60% or greater, most preferably 70% or 80% or 90% or greater) of their maximum serum concentration for any given dose.

The term "effective amount" or "pharmaceutically effective amount" refer to the amount and/or dosage, and/or dosage regime of one or more compounds necessary to bring about the desired result e.g., an amount sufficient to mitigating in a mammal one or more symptoms associated with mild cognitive impairment (MCI), or an amount sufficient to lessen the severity or delay the progression of a disease characterized by amyloid deposits in the brain in a mammal (e.g., therapeutically effective amounts), an amount sufficient to reduce the risk or delaying the onset, and/or reduce the ultimate severity of a disease characterized by amyloid deposits in the brain in a mammal (e.g., prophylactically effective amounts).

The phrase "cause to be administered" refers to the actions taken by a medical professional (e.g., a physician), or a person controlling medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like.

The phrase "in conjunction with" when used in reference to the use of the active agent(s) described herein (e.g., one or more of tropisetron, disulfuram, honokiol and nimetazepam, or an analogue thereof, an enantiomer, a mixture of enantiomers, a pharmaceutically acceptable salt, solvate, or hydrate of said compound(s) or analogue(s)) in conjunction with one or more other drugs described herein (e.g., an acetylcholinesterase inhibitor) the active agent(s) and the other drug(s) are administered so that there is at least some chronological overlap in their physiological activity on the organism. When they are not administered in conjunction with each other, there is no chronological overlap in physiological activity on the organism. In certain preferred embodiments, the "other drug(s)" are not administered at all (e.g., not co-administered) to the organism.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease. In certain embodiments, the reduction or elimination of one or more symptoms of pathology or disease can include, but is not limited to, reduction or elimination of one or more markers that are characteristic of the pathology or disease (e.g., of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, sAPPα/Aβ42 ratio, etc.) and/or reduction, stabilization or reversal of one or more diagnostic criteria (e.g., clinical dementia rating (CDR)).

As used herein, the phrase "consisting essentially of" refers to the genera or species of active pharmaceutical agents recited in a method or composition, and further can include other agents that, on their own do not substantial activity for the recited indication or purpose. In some embodiments, the phrase "consisting essentially of" expressly excludes the inclusion of one or more additional agents that have neuropharmacological activity other than the recited compounds (e.g., other than tropisetron, disulfuram, honokiol and/or nimetazepam). In some embodiments, the phrase "consisting essentially of" expressly excludes the inclusion of one or more additional active agents other than the compounds (e.g., other than tropisetron, disulfuram, honokiol and/or nimetazepam).). In some embodiments, the phrase "consisting essentially of" expressly excludes the inclusion of one or more acetylcholinesterase inhibitors.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

DETAILED DESCRIPTION

1. Introduction

Figure 1:
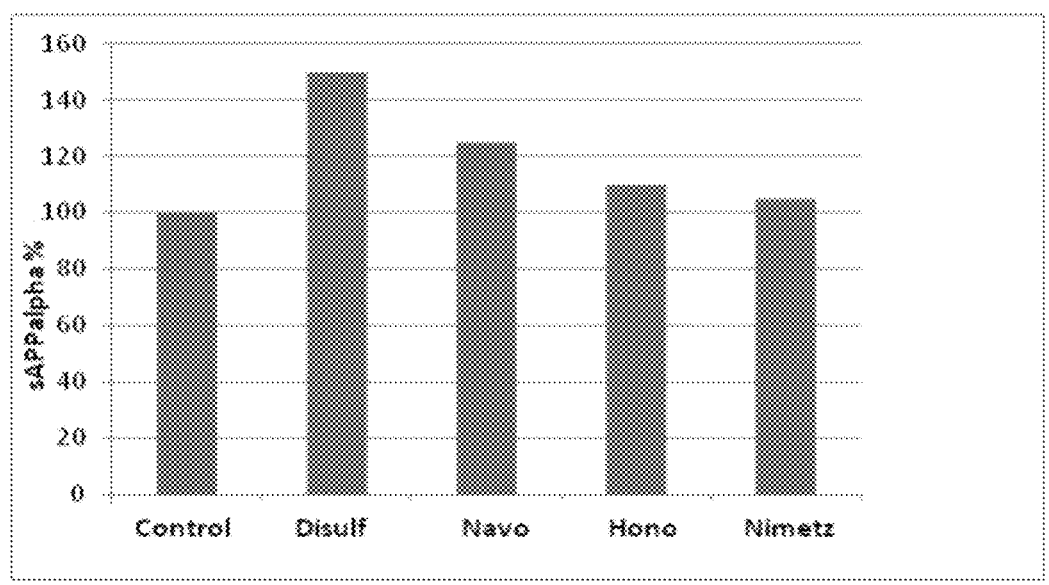
FIG. 1 illustrates a screening assay using 7 W cells stably transfected with wild-type APP and exposed to the compounds (e.g., tropisetron (Navo), disulfuram (Disulf), honokiol (Hono) and nimetazepam (Nimetz)).

The methods described herein are based, in part, on the surprising discovery that certain compounds (e.g., tropisetron, disulfuram, honokiol and nimetazepam, and various pharmaceutical forms thereof) promote processing of amyloid beta (A4) precursor protein ("APP") by the nonamyloidogenic ("anti-AD") pathway and reduces or inhibit processing of APP by the amyloidogenic ("pro-AD") pathway. This is believed to result in reduced production of Aβ, which may be deposited in amyloid plaques in the brain and the other pro-amyloidogenic fragments known to result in neurotoxicity.

Moreover, it is believed that these compounds can be used to mitigate or ameliorate in a mammal one or more symptoms associated with mild cognitive impairment (MCI), particular MCI associated with amyloid deposits in the brain.

Accordingly, in various embodiments methods are provided for the treatment and/or prevention of diseases characterized by an amyloidogenic process (e.g., MCI or the progression of MCI to Alzheimer's disease). The methods involve administration of one or more compounds (e.g., tropisetron, disulfuram, honokiol, and/or nimetazepam) and/or an analog thereof for the prevention and/or treatment of diseases characterized by amyloid deposits in the brain, particularly MCI or the progression of MCI to early stage Alzheimer's disease. In certain embodiments the compounds can be used to ameliorate one or more symptoms of Alzheimer's disease as described herein.

2. Subjects Who can Benefit from the Present Methods

While the methods described herein are detailed primarily in the context of mild cognitive impairment (MCI) and Alzheimer's disease (AD) it is believed they can apply equally to other pathologies characterized by amyloidosis. Illustrative, but non-limiting list of conditions characterized by amyloid plaque formation are shown in Table 1.

TABLE 1

Illustrative pathologies characterized by amyloid formation/deposition.

| Disease | Characteristic Protein | Abbreviation |
|---|---|---|
| Alzheimer's disease | Beta amyloid | Aβ |
| Diabetes mellitus type 2 | Islet amyloid protein (Amylin) | IAPP |
| Parkinson's disease | Alpha-synuclein | SNCA |
| Transmissible spongiform encephalopathy e.g. Bovine spongiform encephalopathy | Prion | PrP |
| Huntington's Disease | Huntingtin | HTT |
| Medullary carcinoma of the thyroid | Calcitonin | ACal |
| Cardiac arrhythmias, Isolated atrial amyloidosis | Atrial natriuretic factor | AANF |
| Atherosclerosis | Apolipoprotein AI | AApoA1 |
| Rheumatoid arthritis | Serum amyloid A | AA |
| Aortic medial amyloid | Medin | AMed |

TABLE 1-continued

Illustrative pathologies characterized by amyloid formation/deposition.

| Disease | Characteristic Protein | Abbreviation |
|---|---|---|
| Prolactinomas | Prolactin | APro |
| Familial amyloid polyneuropathy | Transthyretin | ATTR |
| Hereditary non-neuropathic systemic amyloidosis | Lysozyme | ALys |
| Dialysis related amyloidosis | Beta 2 microglobulin | Aβ2M |
| Finnish amyloidosis | Gelsolin | AGel |
| Lattice corneal dystrophy | Keratoepithelin | AKer |
| Cerebral amyloid angiopathy | Beta amyloid[15] | Aβ |
| Cerebral amyloid angiopathy (Icelandic type) | Cystatin | ACys |
| systemic AL amyloidosis | Immunoglobulin light chain AL | AL |
| Sporadic Inclusion Body Myositis | S-IBM | none |
| Age-related macular degeneration (AMD) | Beta amyloid | Aβ |
| Cerebrovascular dementia | Cerebrovascular amyloid | CVA |

Subjects/patients amenable to treatment using the methods described herein include individuals at risk of disease (e.g., a pathology characterized by amyloid plaque formation such as MCI) but not showing symptoms, as well as subjects presently showing symptoms. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein present methods are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, mutations in the APP gene, particularly mutations at position 717 and positions 670 and 671 referred to as the Hardy and Swedish mutations respectively (see Hardy (1997) *Trends. Neurosci.*, 20: 154-159). Other markers of risk include mutations in the presenilin genes (PS1 and PS2), family history of AD, having the familial Alzheimer's disease (FAD) mutation, the APOE ε4 allele, hypercholesterolemia or atherosclerosis. Further susceptibility genes for the development of Alzheimer's disease are reviewed, e.g., in Sleegers, et al. (2010) *Trends Genet.* 26(2): 84-93.

In some embodiments, the subject is asymptomatic but has familial and/or genetic risk factors for developing MCI or Alzheimer's disease. In asymptomatic patients, treatment can begin at any age (e.g., 20, 30, 40, 50 years of age). Usually, however, it is not necessary to begin treatment until a patient reaches at least about 40, 50, 60 or 70 years of age.

In some embodiments, the subject is exhibiting symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/Aβ40 ratio, and sAPPα/Aβ42 ratio signify the presence of AD. In some embodiments, the subject or patient is diagnosed as having MCI. Increased levels of neural thread protein (NTP) in urine and/or increased levels of α2-macroglobulin (α2M) and/or complement factor H(CFH) in plasma are also biomarkers of MCI and/or AD. See, Anoop, et al., *Int J Alzheimers Dis.* (2010) Jun. 23; 2010. pii: 606802 (PMID 20721349). In some embodiments, the subject or patient is diagnosed as having Alzheimer's disease (e.g., early-stage, mid-stage or late-stage).

In certain embodiments, subjects amenable to treatment may have age-associated memory impairment (AAMI), or mild cognitive impairment (MCI). The methods described herein are particularly well-suited to the treatment of MCI. In such instances, the methods can reduce one or more symptoms characteristic of MCI and/or delay or prevent the progression from MCI to early-, mid- or late-stage Alzheimer's disease or reduce the ultimate severity of the disease.

Mild Cognitive Impairment (MCI)

Mild cognitive impairment (MCI, also known as incipient dementia, or isolated memory impairment) is a diagnosis given to individuals who have cognitive impairments beyond that expected for their age and education, but that typically do not interfere significantly with their daily activities (see, e.g., Petersen et al. (1999) *Arch. Neurol.* 56(3): 303-308). It is considered in many instances to be a boundary or transitional stage between normal aging and dementia. Although MCI can present with a variety of symptoms, when memory loss is the predominant symptom it is termed "amnestic MCI" and is frequently seen as a risk factor for Alzheimer's disease (see, e.g., Grundman et al. (2004) *Arch. Neurol.* 61(1): 59-66; and on the internet at en.wikipedia.org/wiki/Mild_cognitive_impairment-cite_note-Grundman-1). When individuals have impairments in domains other than memory it is often classified as non-amnestic single- or multiple-domain MCI and these individuals are believed to be more likely to convert to other dementias (e.g. dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al. (2006) *Arch. Neurol.* 63(5): 665-72).

The diagnosis of MCI typically involves a comprehensive clinical assessment including clinical observation, neuroimaging, blood tests and neuropsychological testing. A similar assessment is usually given for diagnosis of Alzheimer's disease. There is emerging evidence that magnetic resonance imaging can observe deterioration, including progressive loss of gray matter in the brain, from mild cognitive impairment to full-blown Alzheimer disease (see, e.g., Whitwell et al. (2008) *Neurology* 70(7): 512-520). A technique known as PiB PET imaging is used to clearly show the sites and shapes of beta amyloid deposits in living subjects using a C11 tracer that binds selectively to such deposits (see, e.g., Jack et al. (2008) *Brain* 131(Pt 3): 665-680).

Presently, MCI is typically diagnosed when there is 1) Evidence of memory impairment; 2) Preservation of general cognitive and functional abilities; and 3) Absence of diagnosed dementia.

MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The necessary information to make each rating is obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 2.

TABLE 2

Illustrative clinical dementia rating (CDR) table.

| | Impairment: | | | | |
| --- | --- | --- | --- | --- | --- |
| | None | Questionable | Mild | Moderate | Severe |
| | CDR: | | | | |
| | 0 | 0.5 | 1 | 2 | 3 |
| Memory | No memory loss or slight inconsistent forgetfulness | Consistent slight forgetfulness; partial recollection of events' "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home | |
| | | | | Appears well enough to be taken to functions outside a family home | Appears too ill to be taken to functions outside a family home. |
| Home and Hobbies | Life at home, hobbies, and intellectual interests | Life at home, hobbies, and intellectual interests | Mild bit definite impairment of function at home; | Only simple chores preserved; very restricted | No significant function in home |

TABLE 2-continued

Illustrative clinical dementia rating (CDR) table.

| | Impairment: | | | | |
|---|---|---|---|---|---|
| | None | Questionable | Mild | Moderate | Severe |
| | | | CDR: | | |
| | 0 | 0.5 | 1 | 2 | 3 |
| | well maintained | slightly impaired | more difficult chores abandoned; more complicated hobbies and interests abandoned | interests, poorly maintained | |
| Personal Care | | Fully capable of self-care | Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In various embodiments administration of one or more agents described herein (e.g., tropisetron, disulfuram, honokiol and nimetazepam, or a pharmaceutically acceptable forms thereof, or an analogue thereof or its pharmaceutically form) is deemed effective when there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al., *Arch Neurol* (2004) 61:59-66 report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemory cognitive measures included in the battery. Tests of learning, attention, perceptual speed, category fluency, and executive function may be impaired in patients with MCI, but these are far less prominent than the memory deficit.

Alzheimer's Disease (AD).

In certain embodiments, the methods described herein useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's Criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al. (1984) *Neurology* 34(7): 939-44. According to these criteria, the presence of cognitive impairment and a suspected dementia syndrome should be confirmed by neuropsychological testing for a clinical diagnosis of possible or probable AD. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al. (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al. (1984) *Am. J. Psychiatr.*, 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al. supra). Any score greater than or equal to 25 points (out of 30) is effectively normal (intact). Below this, scores can indicate severe ($\leq 9$ points), moderate (10-20 points) or mild (21-24 points) Alzheimer's disease.

Alzheimer's disease can be broken down into various stages including: 1) Moderate cognitive decline (Mild or early-stage Alzheimer's disease), 2) Moderately severe cognitive decline (Moderate or mid-stage Alzheimer's disease), 3) Severe cognitive decline (Moderately severe or mid-stage Alzheimer's disease), and 4) Very severe cognitive decline (Severe or late-stage Alzheimer's disease) as shown in Table 3.

TABLE 3

Illustrative stages of Alzheimer's disease.

Moderate Cognitive Decline (Mild or early stage AD)

At this stage, a careful medical interview detects clear-cut deficiencies in the following areas:
Decreased knowledge of recent events.
Impaired ability to perform challenging mental arithmetic. For example, to count backward from 100 by 7s.
Decreased capacity to perform complex tasks, such as marketing, planning dinner for guests, or paying bills and managing finances.
Reduced memory of personal history.
The affected individual may seem subdued and withdrawn, especially in socially or mentally challenging situations.
Moderately severe cognitive decline
(Moderate or mid-stage Alzheimer's disease)

Major gaps in memory and deficits in cognitive function emerge. Some assistance with day-to-day activities becomes essential. At this stage, individuals may:
Be unable during a medical interview to recall such important details as their current address, their telephone number, or the name of the college or high school from which they graduated.
Become confused about where they are or about the date, day of the week or season.
Have trouble with less challenging mental arithmetic; for example, counting backward from 40 by 4s or from 20 by 2s.
Need help choosing proper clothing for the season or the occasion.
Usually retain substantial knowledge about themselves and know their own name and the names of their spouse or children.
Usually require no assistance with eating or using the toilet.
Severe cognitive decline (Moderately
severe or mid-stage Alzheimer's disease)

Memory difficulties continue to worsen, significant personality changes may emerge, and affected individuals need extensive help with daily activities. At this stage, individuals may:
Lose most awareness of recent experiences and events as well as of their surroundings.
Recollect their personal history imperfectly, although they generally recall their own name.
Occasionally forget the name of their spouse or primary caregiver but generally can distinguish familiar from unfamiliar faces.
Need help getting dressed properly; without supervision, may make such errors as putting pajamas over daytime clothes or shoes on wrong feet.
Experience disruption of their normal sleep/waking cycle.
Need help with handling details of toileting (flushing toilet, wiping and disposing of tissue properly).

TABLE 3-continued

Illustrative stages of Alzheimer's disease.

Have increasing episodes of urinary or fecal incontinence.
Experience significant personality changes and behavioral symptoms, including suspiciousness and delusions (for example, believing that their caregiver is an impostor); hallucinations (seeing or hearing things that are not really there); or compulsive, repetitive behaviors such as hand-wringing or tissue shredding.
Tend to wander and become lost.
Very severe cognitive decline (Severe or late-stage Alzheimer's disease)

This is the final stage of the disease when individuals lose the ability to respond to their environment, the ability to speak, and, ultimately, the ability to control movement.
Frequently individuals lose their capacity for recognizable speech, although words or phrases may occasionally be uttered.
Individuals need help with eating and toileting and there is general incontinence.
Individuals lose the ability to walk without assistance, then the ability to sit without support, the ability to smile, and the ability to hold their head up. Reflexes become abnormal and muscles grow rigid.
Swallowing is impaired.

In various embodiments administration of one or more agents described herein to subjects diagnosed with Alzheimer's disease is deemed effective when the there is a reduction in the CSF of levels of one or more components selected from the group consisting of Tau, phospho-Tau (pTau), APPneo, soluble A$\beta$40, soluble A$\beta$42, and/or and A$\beta$42/A$\beta$40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments Subjects amenable to the present methods generally are free of a neurological disease or disorder other than Alzheimer's disease. For example, in certain embodiments, the subject does not have and is not at risk of developing a neurological disease or disorder such as Parkinson's disease, and/or schizophrenia, and/or psychosis.

3. Compounds for Administration

The methods described herein are based, in part, on the discovery that administration of one or more compounds (e.g., tropisetron, disulfuram, honokiol, and/or nimetazepam or their pharmaceutically acceptable forms), and/or analogs thereof, and/or pharmaceutically acceptable forms thereof, finds use in the treatment and prevention of diseases characterized by amyloid deposits in the brain, for example, Alzheimer's disease.

Tropisetron, (ADDN-F03) is also known as (1R,5S)-8-methyl-8-azabicyclo[3.2.1] octan-3-yl 1methyl-indole-3-carboxylate, and referenced as CAS number 89565-68-4, or CAS number 105826-92-4. Tropisetron hydrochloride, and other pharmaceutically acceptable salts, as described herein, acts as both a selective 5-HT3 receptor antagonist and a partial $\alpha$7-nicotinic receptor agonist. Macor, et al., *Bioorganic & Medicinal Chemistry Letters* (2001) 11 (3): 319-21; and Cui, et al., *European Journal of Pharmacology* (2009) 609 (1-3): 74-7. The chemical structure of tropisetron is depicted below in Formula I:

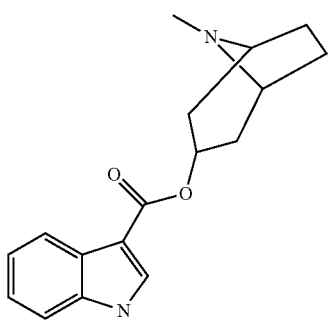

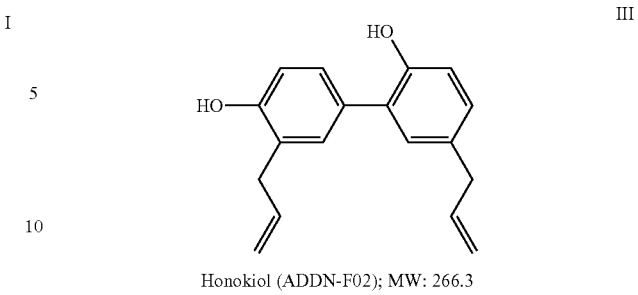

Honokiol (ADDN-F02); MW: 266.3

Analogs of honokiol are known in the art and find use in the present methods. Illustrative analogs of honokiol that find use are described, e.g., in Kuribara, et al., *Pharmacol Biochem Behav.* (2000) 67(3):597-601; Luo, et al., *Bioorganic & Medicinal Chemistry Letters*, (2009) 19(16):4702-4705; Esumi, et al., *Bioorganic & Medicinal Chemistry Letters* (2004) 14(10): 2621-2625; Ahn, et al., *Mol Cancer Res* (2006) 4:621; Fried, et al., *Antioxid Redox Signal.* (2009) 11(5):1139-1148; and WO 2008/137420.

Nimetazepam, also known as 2-methyl-9-nitro-6-phenyl-2,5-diazabicyclo[5.4.0] undeca-5,8,10,12-tetraen-3-one, and referenced as CAS number 2011-67-8, is a benzodiazepine derivative possessing hypnotic, anxiolytic, sedative, skeletal muscle relaxant, and anticonvulsant properties. The chemical structure of nimetazepam is depicted below in Formula IV:

Analogs of tropisetron are known in the art and find use in the present methods. Illustrative analogs of tropisetron that find use are described, e.g., in U.S. Pat. Nos. 4,789,673 and 5,998,429, hereby incorporated herein by reference in their entirety for all purposes, in particular for the compounds described therein. Preferred analogs promote the processing of APP by the nonamyloidogenic pathway. Assays for testing the functional ability of a tropisetron analog to promote the processing of APP by the nonamyloidogenic pathway are known in the art and described herein.

Disulfuram, also known as 1,1',1'',1'''-[disulfanediylbis(carbonothioylnitrilo)]tetraethane or 1-(diethylthiocarbamoyldisulfanyl)-N,N-diethyl-methanethioamide, and referenced as CAS number 97-77-8, prevents the breakdown of dopamine and has anti-protozoal activity. It is used to support the treatment of chronic alcoholism by producing an acute sensitivity to alcohol. The chemical structure of tropisetron is depicted below in Formula II:

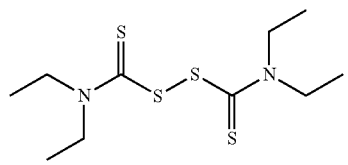

Disulfiram (ADDN-F01); MW: 295.3

Analogs of disulfuram are known in the art and find use in the present methods. Illustrative analogs of disulfuram that find use are described, e.g., in Kitson, *Biochem J* (1976) 155:445-448 and Fowler, et al., *Biochem. J.* (1993) 289: 853-859. Additional disulfuram analogs that find use include methylenethiuram disulfide (Labar, et al., *ChemBioChem* (2007) 8(11): 1293-1297); tetramethylthiuram disulphide, (Strömme, et al., *Biochemical Pharmacology* (1965) 14(4): 381-391); and pyrrolidine dithiocarbamate (PDTC) (Wickström, et al., *Biochemical Pharmacology* (2007) 73(1):25-33.

Honokiol, also known as 2-(4-hydroxy-3-prop-2-enylphenyl)-4-prop-2-enyl-phenol, and referenced as CAS number 35354-74-6, is a biphenolic compound having anxiolytic, antithrombotic, anti-depressant, anti-emetic, antibacterial, anti-tumorigenic and neurotrophic activities. The chemical structure of honokiol is depicted below in Formula III:

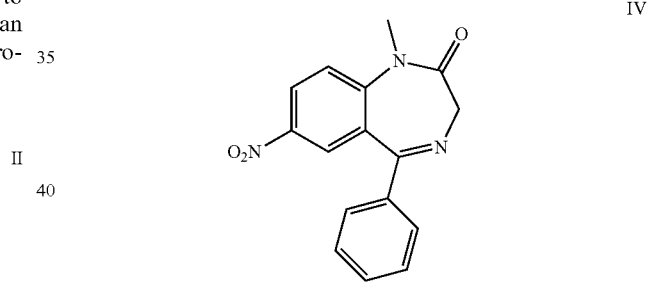

Nimetazepam (ADDN-F04); MW: 295.3

Analogs of nimetazepam are known in the art and find use in the present methods. Illustrative analogs of nimetazepam that find use include other benzodiazepines. Diazepines having a nitro group at position 7 in the 1,4-benzodiazepine structure, e.g., nitrazepam, clonazepam and flunitrazepam are of particular interest. Other benzodiazepines, including without limitation, oxazepam, diazepam and chlordiazepoxide, also find use.

4. Methods of Prevention

For the purposes of prophylaxis, the subject may be asymptomatic, but have one or more environmental, lifestyle or genetic risk factors, as described herein, and/or be of a defined threshold age. Subjects may also be asymptomatic but judged to be at high risk for AD based on genetic tests (e.g., ApoE4 or other AD-associated mutations), imaging tests (e.g., Pittsburgh Compound B scan (PIB scan) or other tests), or other predictive tests known in the art. Alternatively, the subject may be exhibiting symptoms of early stages of disease, e.g., exhibiting symptoms of mild cognitive impairment (MCI) or be diagnosed as having MCI. In such cases, administration of the compound (e.g., tropisetron, disulfuram, honokiol, and/or nimetazepam) and/or an analog thereof can prevent or delay onset of disease or progression of MCI into later stages of disease, e.g., progression to Alzheimer's disease, and/or reduce the severity of the disease once present.

Measurable parameters for evaluating the effectiveness of the prevention regime are as discussed herein for therapy and monitoring.

5. Methods of Treatment

In various methods of treatment, the subject may already exhibit symptoms of disease or be diagnosed as having disease. For example, the subject may exhibit symptoms of MCI or be diagnosed as having MCI. In some embodiments, the subject may exhibit symptoms of Alzheimer's disease or be diagnosed as having Alzheimer's disease. In such cases, administration of the compound (e.g., tropisetron, disulfuram, honokiol, and/or nimetazepam) and/or analogs thereof can reverse or delay progression of and or reduce the severity of disease symptoms.

Measurable parameters for evaluating the effectiveness of the treatment regime are as discussed herein for therapy and monitoring.

6. Formulation and Administration a. Formulation

The compound (e.g., tropisetron, disulfuram, honokiol, and/or nimetazepam) and/or an analog thereof can be administered orally, parenterally, (intravenously (IV), intramuscularly (IM), depo-IM, subcutaneously (SQ), and depo-SQ), sublingually, intranasally (inhalation), intrathecally, transdermally (e.g., via transdermal patch), topically, ionophoretically or rectally. Typically the dosage form is selected to facilitate delivery to the brain (e.g., passage through the blood brain barrier). In this context it is noted that the compounds described herein are readily delivered to the brain. Dosage forms known to those of skill in the art are suitable for delivery of the compound.

Compositions are provided that contain therapeutically effective amounts of the compound. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

These active agents (e.g., tropisetron, disulfuram, honokiol, and/or nimetazepamand/or analogs thereof) can be administered in the "native" form or, if desired, in the form of salts, esters, amides, prodrugs, derivatives, and the like, provided the salt, ester, amide, prodrug or derivative is suitable pharmacologically effective, e.g., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure*, 4th Ed. N.Y. Wiley-Interscience.

Methods of formulating such derivatives are known to those of skill in the art. For example, the disulfide salts of a number of delivery agents are described in PCT Publication WO 2000/059863 which is incorporated herein by reference. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, orotic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

For the preparation of salt forms of basic drugs, the pKa of the counterion is preferably at least about 2 pH lower than the pKa of the drug. Similarly, for the preparation of salt forms of acidic drugs, the pKa of the counterion is preferably at least about 2 pH higher than the pKa of the drug. This permits the counterion to bring the solution's pH to a level lower than the pHmax to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (e.g., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysine, magnesium, meglumine, potassium, procaine, sodium, tromethamine, zinc, and the like.

In various embodiments preparation of esters typically involves functionalization of hydroxyl and/or carboxyl groups that are present within the molecular structure of the active agent. In certain embodiments, the esters are typically acyl-substituted derivatives of free alcohol groups, e.g., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

About 1 to 1000 mg of a compound or mixture of the compound (e.g., tropisetron, disulfuram, honokiol, and/or nimetazepam) or a physiologically acceptable salt or ester is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 1-1000 mg, 2-800 mg, 5-500 mg, 10-400 mg, 50-200 mg, e.g., about 5 mg, 10 mg, 15 mg, 20 mg, 25 mg, 30 mg, 35 mg, 40 mg, 45 mg, 50 mg, 60 mg, 70 mg, 80 mg, 90 mg, 100 mg, 200 mg, 300 mg, 400 mg, 500 mg, 600 mg, 700 mg, 800 mg, 900 mg or 1000 mg of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare compositions, the compound is mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween™, and dissolution in aqueous sodium bicarbonate. Derivatives of the compounds, such as salts or prodrugs may also be used in formulating effective pharmaceutical compositions.

The concentration of the compound is effective for delivery of an amount upon administration that lessens or ameliorates at least one symptom of the disorder for which the compound is administered and/or that is effective in a prophylactic context. Typically, the compositions are formulated for single dosage (e.g., daily) administration.

The compounds may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo model systems for the treated disorder. A therapeutically or prophylactically effective dose can be determined by first administering a low dose, and then incrementally increasing until a dose is reached that achieves the desired effect with minimal or no undesired side effects.

In various embodiments, the compounds and/or analogs thereof can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for co-administration. The inhibitor and second therapeutic agent may be provided as separate component parts. A kit may include a plurality of containers, each container holding one or more unit dose of the compounds. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration.

The concentration and/or amount of active compound in the drug composition will depend on absorption, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound can be provided in a formulation that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

In various embodiments, the tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

b. Routes of Administration and Dosing

In various embodiments, the compounds and/or analogs thereof can be administered orally, parenterally (IV, IM, depo-IM, SQ, and depo-SQ), sublingually, intranasally (inhalation), intrathecally, transdermally (e.g., via transdermal patch), topically, or rectally. Dosage forms known to those skilled in the art are suitable for delivery of the compounds and/or analogs thereof.

In various embodiments, the compounds and/or analogs thereof may be administered enterally or parenterally. When administered orally, the compounds can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compound needs to be administered only once or twice daily.

The oral dosage forms can be administered to the patient 1, 2, 3, or 4 times daily. It is preferred that the compound be administered either three or fewer times, more preferably once or twice daily. Hence, it is preferred that the compound be administered in oral dosage form. It is preferred that whatever oral dosage form is used, that it be designed so as to protect the compound from the acidic environment of the stomach. Enteric coated tablets are well known to those skilled in the art. In addition, capsules filled with small spheres each coated to protect from the acidic stomach, are also well known to those skilled in the art.

When administered orally, an administered amount therapeutically effective to inhibit amyloidogenic processing of APP, promote non-amyloidogenic processing of APP, or to treat or prevent AD is from about 0.1 mg/day to about 200 mg/day, for example, from about 1 mg/day to about 100 mg/day, for example, from about 5 mg/day to about 50 mg/day. In some embodiments, the subject is administered the compound at a dose of about 0.05 to about 0.50 mg/kg, for example, about 0.05 mg/kg, 0.10 mg/kg, 0.20 mg/kg, 0.33 mg/kg, 0.50 mg/kg. It is understood that while a patient may be started at one dose, that dose may be varied (increased or decreased, as appropriate) over time as the patient's condition changes. Depending on outcome evaluations, higher doses may be used. For example, in certain embodiments, up to as much as 1000 mg/day can be administered, e.g., 5 mg/day, 10 mg/day, 25 mg/day, 50 mg/day, 100 mg/day, 200 mg/day, 300 mg/day, 400 mg/day, 500 mg/day, 600 mg/day, 700 mg/day, 800 mg/day, 900 mg/day or 1000 mg/day.

The compounds and/or analogs thereof may also be advantageously delivered in a nano crystal dispersion formulation. Preparation of such formulations is described, for example, in U.S. Pat. No. 5,145,684. Nano crystalline dispersions of HIV protease inhibitors and their method of use are described in U.S. Pat. No. 6,045,829. The nano crystalline formulations typically afford greater bioavailability of drug compounds.

In various embodiments, the compounds and/or analogs thereof can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

In various embodiments, the compounds and/or analogs thereof can be administered sublingually. When given sublingually, the compounds and/or analogs thereof can be given one to four times daily in the amounts described above for IM administration.

In various embodiments, the compounds and/or analogs thereof can be administered intranasally. When given by this route, the appropriate dosage forms are a nasal spray or dry powder, as is known to those skilled in the art. The dosage of compound and/or analog thereof for intranasal administration is the amount described above for IM administration.

In various embodiments, compound and/or analogs thereof can be administered intrathecally. When given by this route the appropriate dosage form can be a parenteral dosage form as is known to those skilled in the art. The dosage of compound and/or analog thereof for intrathecal administration is the amount described above for IM administration.

In certain embodiments, the compound and/or analog thereof can be administered topically. When given by this route, the appropriate dosage form is a cream, ointment, or patch. When administered topically, the dosage is from about 1.0 mg/day to about 200 mg/day. Because the amount that can be delivered by a patch is limited, two or more patches may be used. The number and size of the patch is not important, what is important is that a therapeutically effective amount of compound be delivered as is known to those skilled in the art. The compound can be administered rectally by suppository as is known to those skilled in the art. When administered by suppository, the therapeutically effective amount is from about 1.0 mg to about 500 mg.

In various embodiments, the compound and/or analog thereof can be administered by implants as is known to those skilled in the art. When administering the compound by implant, the therapeutically effective amount is the amount described above for depot administration.

It should be apparent to one skilled in the art that the exact dosage and frequency of administration will depend on the particular condition being treated, the severity of the condition being treated, the age, weight, general physical condition of the particular patient, and other medication the individual may be taking as is well known to administering physicians who are skilled in this art.

7. Combination Therapies

In certain embodiments, the compounds and/or analogs thereof (e.g., tropisetron, disulfuram, honokiol and/or nimetazepam or analogues thereof) can be used in combination with other therapeutic agents or approaches used to treat or prevent diseases characterized by amyloid deposits in the brain, including MCI and/or AD. Such agents or approaches include: acetylcholinesterase inhibitors (including without limitation, e.g., (−)-phenserine enantiomer, tacrine, ipidacrine, galantamine, donepezil, icopezil, zanapezil, rivastigmine, huperzine A, phenserine, physostigmine, neostigmine, pyridostigmine, ambenonium, demarcarium, edrophonium, ladostigil and ungeremine); NMDA receptor antagonist (including without limitations e.g., Memantine); muscarinic receptor agonists (including without limitation, e.g., Talsaclidine, AF-102B, AF-267B (NGX-267)); nicotinic receptor agonists (including without limitation, e.g., Ispronicline (AZD-3480)); beta-secretase inhibitors (including without limitations e.g., thiazolidinediones, including rosiglitazone and pioglitazone); gamma-secretase inhibitors (including without limitation, e.g., MK-0752, E-2012, BMS-708163, PF-3084014, begacestat (GSI-953), and NIC5-15); inhibitors of Aβ aggregation (including without limitation, e.g., Clioquinol (PBT1), PBT2, tramiprosate (homotaurine), Scyllo-inositol (a.k.a., scyllo-cyclohexanehexyl, AZD-103 and ELND-005), passive immunotherapy with Aβ fragments (including without limitations e.g., Bapineuzemab) and Epigallocatechin-3-gallate (EGCg)); anti-inflammatory agents such as cyclooxygenase II inhibitors; anti-oxidants such as Vitamin E and ginkolides; immunological approaches, such as, for example, immunization with Aβ peptide or administration of anti-Aβ peptide antibodies; statins; and direct or indirect neurotrophic agents such as Cerebrolysin™, AIT-082 (Emilieu, 2000, *Arch. Neurol.* 57:454), Netrin (Luorenco, 2009, *Cell Death Differ* 16, 655-663), Netrin mimetics, NGF, NGF mimetics, BDNF and other neurotrophic agents of the future, agents that promote neurogenesis e.g. stem cell therapy and/or gene therapy. Further pharmacologic agents useful in combination with tropisetron, disulfuram, honokiol and/or nimetazepam to treat or prevent diseases characterized by amyloid deposits in the brain, including MCI and/or AD, are described, e.g., in Mangialasche, et al., *Lancet Neurol* (2010) 9:702-16.

In various embodiments, combination therapy with tropisetron, disulfuram, honokiol and/or nimetazepam expressly excludes administration of tropisetron, disulfuram, honokiol and/or nimetazepam in conjunction with an acetylcholinesterase inhibitor. In some embodiments, tropisetron is not administered in conjunction with an acetylcholinesterase inhibitor.

8. Assay Systems to Evaluate APP Processing

Without being bound to a particular theory, it is believed that the compounds (e.g., tropisetron, disulfuram, honokiol and/or nimetazepam) and/or analogs thereof promote processing of APP by the nonamyloidogenic pathway and/or reduce or inhibits processing of APP by the amyloidogenic pathway. In the nonamyloidogeic pathway, APP is first cleaved by a-secretase within the Aβ sequence, releasing the APPsα ectodomain ("sAPPα"). In contrast, the amyloidogenic pathway is initiated when β-secretase cleaves APP at the amino terminus of the Aβ, thereby releasing the APPsβ ectodomain ("sAPPβ"). APP processing by the nonamyloidogenic and amyloidogenic pathways is known in the art and reviewed, e.g., by Xu, *J Alzheimers Dis* (2009) 16(2): 211-224 and De Strooper, et al., *Nat Rev Neurol* (2010) 6(2):99-107.

One method to evaluate the efficacy of the compounds and/or analogs thereof is to determine a reduction or elimination in the level of APP processing by the amyloidogenic pathway, e.g., a reduction or elimination in the level of APP processing by β-secretase cleavage in response to the administration of the compound(s) of interest. Assays for determining the extent of APP cleavage at the β-secretase cleavage site are well known in the art. Illustrative assays are described, for example, in U.S. Pat. Nos. 5,744,346 and 5,942,400. Kits for determining the presence and levels in a biological sample of sAPPα and sAPPβ, as well as APPneo and Aβ commercially available, e.g., from PerkinElmer.

a. Cell Free Assays

Illustrative assays that can be used to demonstrate the inhibitory activity of the compound and/or analogs thereof are described, for example, in WO 00/17369, WO 00/03819, and U.S. Pat. Nos. 5,942,400 and 5,744,346. Such assays can be performed in cell-free incubations or in cellular incubations using cells expressing an alpha-secretase and/or beta-secretase and an APP substrate having a alpha-secretase and beta-secretase cleavage sites.

In one illustrative embodiment, the compound(s) of interest are contacted with an APP substrate containing alpha-secretase and beta-secretase cleavage sites of APP, for example, a complete APP or variant, an APP fragment, or a recombinant or synthetic APP substrate containing the amino acid sequence: KM-DA or NL-DA (APP-SW), is incubated in the presence of an alpha-secretase and/or beta-secretase enzyme, a fragment thereof, or a synthetic or recombinant polypeptide variant having alpha-secretase or beta-secretase activity and effective to cleave the alpha-secretase or beta-secretase cleavage sites of APP, under incubation conditions suitable for the cleavage activity of the enzyme. Compounds having the desired activity reduce or prevent cleavage of the APP substrate. Suitable substrates optionally include derivatives that may be fusion proteins or peptides that contain the substrate peptide and a modification useful to facilitate the purification or detection of the peptide or its alpha-secretase and/or beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar of the compound, in aqueous solution, at an approximate pH of 4-7, at approximately 37° C., for a time period of approximately 10 minutes to 3 hours. These incubation conditions are exemplary only, and can be varied as required for the particular assay components and/or desired measurement system. Optimization of the incubation conditions for the particular assay components should account for the specific alpha-secretase and/or beta-secretase enzyme used and its pH optimum, any additional enzymes and/or markers that might be used in the assay, and the like. Such optimization is routine and will not require undue experimentation.

Another illustrative assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of alpha-secretase and/or beta-secretase results in cleavage of the substrate at the alpha-secretase and/or beta-secretase cleavage sites, respectively. This system can be used to screen for the inhibitory activity of the compounds of interest. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

b. Cellular Assays

Numerous cell-based assays can be used to evaluate the activity of compound(s) of interest on relative alpha-secretase activity to beta-secretase activity and/or processing of APP to release amyloidogenic versus non-amyloidogenic Aβ oligomers. Contact of an APP substrate with an alpha-secretase and/or beta-secretase enzyme within the cell and in the presence or absence of the compound and/or analog thereof can be used to demonstrate alpha-secretase promoting and/or beta-secretase inhibitory activity of the compound or analog thereof. Preferably, the assay in the presence of the compound or analog thereof provides at least about 30%, most preferably at least about 50% inhibition of the beta-secretase enzymatic activity, as compared with a non-inhibited control. In other embodiments, the assay in the presence of the compound or analog thereof provides at least about 30%, most preferably at least about 50% increase of the alpha-secretase enzymatic activity, as compared with a control assay in the absence of the compound.

In one embodiment, cells that naturally express alpha-secretase and/or beta-secretase are used. Alternatively, cells are modified to express a recombinant alpha-secretase and/or beta-secretase or synthetic variant enzymes, as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the alpha-secretase and/or beta-secretase APP cleavage sites can be used, provided that the expressed APP is permitted to contact the enzyme and enzymatic cleavage activity can be analyzed.

Human cell lines that normally process Aβ from APP provide a useful means to assay inhibitory activities of the compounds. Production and release of Aβ and/or other cleavage products into the culture medium can be measured, for example by immunoassay, such as Western blot or enzyme-linked immunoassay (EIA) such as by ELISA.

Cells expressing an APP substrate and an active alpha-secretase and/or beta-secretase can be incubated in the presence of the compound to demonstrate relative enzymatic activity of the alpha-secretase and/or beta-secretase as compared with a control. Relative activity of the alpha-secretase to the beta-secretase can be measured by analysis of one or more cleavage products of the APP substrate. For example, inhibition of beta-secretase activity against the substrate APP would be expected to decrease release of specific beta-secretase induced APP cleavage products such as Aβ, sAPPβ and APPneo. Promotion or enhancement of alpha-secretase activity against the substrate APP would be expected to increase release of specific alpha-secretase induced APP cleavage products such as sAPPα and p3 peptide.

Although both neural and non-neural cells process and release Aβ, levels of endogenous beta-secretase activity are low and often difficult to detect by EIA. The use of cell types known to have enhanced beta-secretase activity, enhanced processing of APP to Aβ, and/or enhanced production of Aβ are therefore preferred. For example, transfection of cells with the Swedish Mutant form of APP (APP-SW); with the Indiana Mutant form (APP-IN); or with APP-SW-IN provides cells having enhanced beta-secretase activity and producing amounts of Aβ that can be readily measured.

In such assays, for example, the cells expressing APP, alpha-secretase and/or beta-secretase are incubated in a culture medium under conditions suitable for alpha-secretase and/or beta-secretase enzymatic activity at its cleavage site on the APP substrate. On exposure of the cells to the compound, the amount of Aβ released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of alpha-secretase and/or beta-secretase activity include primary human neuronal cells, primary transgenic animal neuronal cells where the transgene is APP, and other cells such as those of a stable 293 cell line expressing APP, for example, APP-SW.

c. In Vivo Assays: Animal Models

Various animal models can be used to analyze the activity of compound(s) of interest on relative alpha-secretase and/or beta-secretase activity and/or processing of APP to release Aβ. For example, transgenic animals expressing APP substrate, alpha-secretase and/or beta-secretase enzyme can be used to demonstrate inhibitory activity of the compound. Certain transgenic animal models have been described, for example, in U.S. Pat. Nos. 5,877,399; 5,612,486; 5,387,742; 5,720,936; 5,850,003; 5,877,015, and 5,811,633, and in Ganes et al., 1995, Nature 373:523. Preferred are animals that exhibit characteristics associated with the pathophysiology of AD. Administration of the compound to the transgenic mice described herein provides an alternative method for demonstrating the inhibitory activity of the compound.

Administration of the compound in a pharmaceutically effective carrier and via an administrative route that reaches the target tissue in an appropriate therapeutic amount is also preferred.

Inhibition of beta-secretase mediated cleavage of APP at the beta-secretase cleavage site and of Aβ release can be analyzed in these animals by measure of cleavage fragments in the animal's body fluids such as cerebral fluid or tissues. Likewise, promotion or enhancement of alpha-secretase mediated cleavage of APP at the alpha-secretase cleavage site and of release of sAPPα can be analyzed in these animals by measure of cleavage fragments in the animal's body fluids such as cerebral fluid or tissues. In certain embodiments, analysis of brain tissues for Aβ deposits or plaques is preferred.

On contacting an APP substrate with an alpha-secretase and/or beta-secretase enzyme in the presence of the compound and/or analog thereof under conditions sufficient to permit enzymatic mediated cleavage of APP and/or release of Aβ from the substrate, desirable compounds and/or analogs thereof are effective to reduce beta-secretase-mediated cleavage of APP at the beta-secretase cleavage site and/or effective to reduce released amounts of Aβ. The compound (s) and/or analog(s) thereof are also preferably effective to enhance alpha-secretase-mediated cleavage of APP at the alpha-secretase cleavage site and to increase released amounts of sAPPα. Where such contacting is the administration of the compound and/or analog thereof to an animal model, for example, as described above, the compound and/or analog thereof is effective to reduce Aβ deposition in brain tissues of the animal, and to reduce the number and/or size of beta amyloid plaques. Where such administration is to a human subject, the compound and/or analog thereof is effective to inhibit or slow the progression of disease characterized by enhanced amounts of Aβ, to slow the progression of AD in the, and/or to prevent onset or development of AD in a patient at risk for the disease.

9. Methods of Monitoring Clinical Efficacy

In various embodiments, the effectiveness of treatment can be determined by comparing a baseline measure of a parameter of disease before administration of the compound (e.g., tropisetron, disulfuram, honokiol, and/or nimetazepam) and/or analogs thereof is commenced to the same parameter one or more timepoints after the compound and/or analog has been administered. One illustrative parameter that can be measured is a biomarker (e.g., a peptide oligomer) of APP processing. Such biomarkers include, but are not limited to increased levels of sAPPα, p3 (Aβ17-42 or Aβ17-40), sAPPβ, soluble Aβ40, and/or soluble Aβ42 in the blood, plasma, serum, urine, mucous or cerebrospinal fluid (CSF). Detection of increased levels of sAPPα and/or p3, and decreased levels of sAPPβ and/or APPneo is an indicator that the treatment is effective. Conversely, detection of decreased levels of sAPPα and/or p3, and/or increased levels of sAPPβ, APPneo, Tau or phospho-Tau (pTau) is an indicator that the treatment is not effective.

Another parameter to determine effectiveness of treatment is the level of amyloid plaque deposits in the brain. Amyloid plaques can be determined using any method known in the art, e.g., as determined by CT, PET, PIB-PET and/or MRI. Administration of the compound (e.g., tropisetron, disulfuram, honokiol, and/or nimetazepam) can result in a reduction in the rate of plaque formation, and even a retraction or reduction of plaque deposits in the brain. Effectiveness of treatment can also be determined by observing a stabilization and/or improvement of cognitive abilities of the subject. Cognitive abilities can be evaluated using any art-accepted method, including for example, Clinical Dementia Rating (CDR), the mini-mental state examination (MMSE) or Folstein test, evaluative criteria listed in the DSM-IV (Diagnostic and Statistical Manual of Mental Disorders, Fourth Edition) or DSM-V, and the like.

Clinical efficacy can be monitored using any method known in the art. Measurable biomarkers to monitor efficacy include, but are not limited to, monitoring blood, plasma, serum, urine, mucous or cerebrospinal fluid (CSF) levels of sAPPα, sAPPβ, Aβ42, Aβ40, APPneo and p3 (e.g., Aβ17-42 or Aβ17-40). Detection of increased levels of sAPPα and/or p3, and decreased levels of sAPPβ and/or APPneo are indicators that the treatment or prevention regime is efficacious. Conversely, detection of decreased levels of sAPPα and/or p3, and increased levels of sAPPβ and/or APPneo are indicators that the treatment or prevention regime is not efficacious. Other biomarkers include Tau and phospho-Tau (pTau). Detection of decreased levels of Tau and pTau are indicators that the treatment or prevention regime is efficacious.

Efficacy can also be determined by measuring amyloid plaque load in the brain. The treatment or prevention regime is considered efficacious when the amyloid plaque load in the brain does not increase or is reduced. Conversely, the treatment or prevention regime is considered inefficacious when the amyloid plaque load in the brain increases. Amyloid plaque load can be determined using any method known in the art, e.g., including CT, PET, PIB-PET and/or MRI.

Efficacy can also be determined by measuring the cognitive abilities of the subject. Cognitive abilities can be measured using any method known in the art. Illustrative tests include assigning a Clinical Dementia Rating (CDR) score or applying the mini mental state examination (MMSE) (Folstein, et al., *Journal of Psychiatric Research* 12 (3): 189-98). Subjects who maintain the same score or who achieve an improved score, e.g., when applying the CDR or MMSE, indicate that the treatment or prevention regime is efficacious. Conversely, subjects who receive a score indicating diminished cognitive abilities, e.g., when applying the CDR or MMSE, indicate that the treatment or prevention regime has not been efficacious.

In certain embodiments, the monitoring methods can entail determining a baseline value of a measurable biomarker or parameter (e.g., amyloid plaque load or cognitive abilities) in a subject before administering a dosage of the compound, and comparing this with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation/ANOVA) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (e.g., more than a standard deviation) is an indicator that treatment should be resumed in the subject.

The tissue sample for analysis is typically blood, plasma, serum, urine, mucous or cerebrospinal fluid from the subject.

EXAMPLES

The following examples are offered to illustrate, but not to limit the claimed invention.

Example 1

ALPHALISA® Assays in 7 W APP Transfected Cells

This example provides experimental methods for measurement sAPPα, Aβ42 and APPneo In vitro compound testing assay: 7 W CHO cells were seeded at 50,000 cells/well in a 96 wells plate for 24 h. Then their medium was changed for fresh medium supplemented with 1 µM compounds (e.g., tropisetron, disulfuram, honokiol, and/or nimetazepam). After 24 h, 20 µl of the medium was added to 2 µl of the complete protease inhibitor with 1 µM EDTA and kept at 4° C. until analysis. 2 µl of that medium was treated with the Perkin Elmer (PE) ALPHALISA® Aβ kit to determine the amount of Aβ42 secreted by the cells in 24 h using the PE-Enspire reader. Another aliquot of 2 µl of the medium was diluted with 50 µl of the PE ALPHALISA® buffer and was treated with the PE ALPHALISA® sAPPα kit to determine the amount of sAPPα secreted by the cells in 24 h. For the assay, 2 µl of the final mixture was treated with the acceptor bead and the donor antibody followed by addition of the donor beads and the ALPHALISA® signal was measured using a PE-Enspire reader. For measurement of APPneo, the 50,000 cells were treated after seeding with fresh medium supplemented with or without the compound, but without fetal bovine serum (FBS), in order to induce the formation of the APPneo fragment. After 24 h the medium was removed, the cells on the bottom of the wells were washed three times with phosphate buffered saline (PBS) and then lysed with 50 µl of the Perkin Elmer ALPHALISA® buffer and with 10% of the complete protease inhibitor with EDTA. The cells were then frozen at −20° C. for 1 h. After defreezing, the cells were kept at 4° C. until analysis. Aliquots of 2 µl of the cell lysate were treated with the PE ALPHALISA® APPneo kit (custom) prepared using the APPneo antibody (Galavan, 2006, *Proc Natl Acad Sci USA*, 103, 7130-7135) to determine the amount of APPneo secreted by the cells in 24 h. The results are shown in FIG. 1.

Example 2

J20 (PDAPP Mouse Model) Primary Neuronal Cells

This example provides experimental methods for measurement of sAPPalpha, Aβ42 and APPneo in primary neuronal cells.

Figure 2:
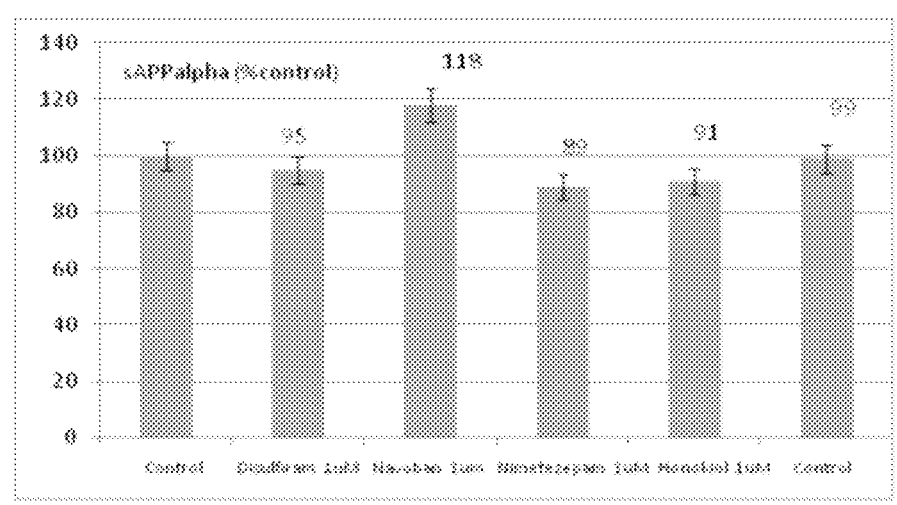
FIGS. 2A-B illustrate the effect of the compounds (e.g., tropisetron, disulfuram, honokiol and nimetazepam) on primary neuronal cultures. Tropisetron is identified as Navoban.
Figure 2:
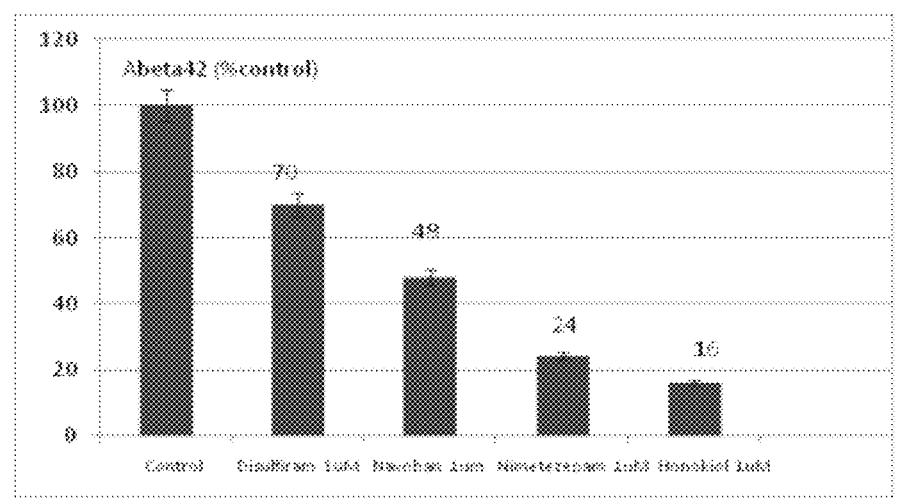

In vitro primary culture compound testing assay: Primary neuronal cultures were made from embryonic 18 day mice J20 hippocampi. The embryos were produced by breeding J20 male and J20 female (both heterozygous)—this gives a 50-75% transgenic culture. Cells were mixed from all embryos and plated at $2\times10^5$ in 6 or more wells (depending on the number of embryos) of a 48 well culture plate previously coated with Poly-L-lysine. Cells were allowed to attach overnight and the compounds (e.g., tropisetron, disulfuram, honokiol, and/or nimetazepam) were added 24 hours after the culture was made. Three wells were used for each compound and a vehicle-only control is always run. The compounds were added to the cells every day for 3 days; on the third day media was collected, protease inhibitors added and the media stored. After a PBS wash, RIPA buffer was added to the cells, they were shaken for 1 min. and then frozen. Aβ42 was immunoprecipitated from the cell media using 4G8 antibody, APPneo was immunoprecipitated from the cells using the APPneo antibody (Galavan, 2006, supra), and sAPPα was directly determined from the media. For some experiments, Aβ42 was also immunoprecipitated from the post-APPneo IP cell supernatant. The results are shown in FIG. 2.

Example 3

Mouse Brain Uptake and Biomarker Studies

This example provides experimental methods for in vivo measurement of compound brain penetration and effect on sAPPalpha, Aβ40/42, and APPneo in the PDAPP mouse model.

Methods

ALPHALISA Analysis: ALPHALISA® kits from Perkin Elmer (PE) were used to quantify sAPPα (cat#: AL254C), sAPPβ (cat#: AL232C), Aβ40 (cat #: AL275C), Aβ42 (cat#: AL276C) and Tau (cat#: AL271C) from brain homogenates. The samples are added to an AlphaPlate-384 (cat#: 6005350). Twenty microliters (µl) of acceptor bead antibody mix was added to each five µl cerebrospinal fluid (CSF) sample and allowed to incubate for one hour at room temperature. Next, 25 µl of donor beads were added and allowed to incubate in the dark for 30 minutes at room temperature. Fluorescence was then measured on an EnsPire 96-well plate reader (Perkin-Elmer).

ELISA assays: ELISA kits from Invitrogen were also used to quantify Aβ1-40 (KHB3481) and Aβ1-42 (KHB3544) in duplicate from the CSF samples stored at −80° C. For assay, samples were thawed on ice and BSL-2 precautions practiced at all times. For the human Aβ 1-42 ultrasensitive ELISA, samples were diluted 1:2 (50 µl CSF plus 50 µl kit-provided standard diluent buffer). For the human Aβ1-40 ELISA, samples were diluted 1:15 (6.7 µl CSF plus 93.8 µl of standard diluent buffer). Assays were performed according to manufacturer's instructions. In short, standards and samples were added to a plate pre-coated with a monoclonal capture antibody specific for the amino terminus of Hu Aβ. The samples were co-incubated with a rabbit detection antibody (Ab) specific for the carboxy terminus of the Aβ species being assayed for 3 hr at room temperature (Aβ 1-40) to overnight at 4° (Aβ 1-42) with gentle rocking After washing, bound rabbit Ab was detected using a horseradish peroxidase-labeled anti-rabbit secondary Ab. After washing again, bound HRP-anti rabbit Ab was detected colorimetrically (Spectramax 190, Molecular Devices) by the addition of a substrate solution. 1 mM 4-(2-Aminoethyl)benzenesulfonyl fluoride hydrochloride (AEBSF) protease inhibitor (101500, Calbiochem) was added to standards and samples.

Brain uptake testing (PK): In general, CNS exposure studies consisted of collection of heparinized plasma and brains after treatment with tropisetron, nimetazepam, disulfuram and honokiol following subcutaneous (sc) administration of the molecules at 10 mg/kg. Plasma and brain levels of the compounds were determined by quantitative LC/MS/MS methodology, conducted at Integrated Analytical Solutions (on the internet at ianalytical.net). Plasma samples were precipitated with acetonitrile:methanol (1:1) cocktail containing an internal standard. The brain samples were homogenized directly in ethylacetate or extracted from 5M guanidine homogenates using the liquid-liquid method. The resulting supernatant were evaporated to dryness and subjected to the LC/MS/MS analysis. For each compound 3 mice were used for analysis. The brain-to-plasma ratios and brain levels were then be calculated to identify the best candidate(s) for further testing.

Aβ40/42, sAPPα and APPneo levels in brain (PD): In general, as part of the CNS exposure studies in Alzheimer's disease transgenic (Tg) mice (e.g., the PDAPP mouse model of Alzheimer's disease), tropisetron, nimetazepam, disulfuram and honokiol effects on biomarkers were also measured. In case of tropisetron the testing was done at 0.3 mpk, while in case of the other compounds (e.g., nimetazepam, disulfuram and honokiol) it was done at 10 mpk. From the collected brains the hippocampi were dissected. Levels of sAPPα, and Aβ1-40, Aβ1-42 and APPneo were measured by ALPHALISA assay (ALPHALISA Perkin-Elmer), and Aβ1-40, Aβ1-42 (Invitrogen, sensitive ELISA kit) in brain homogenates of Tg mice. All procedures involved have been described (Galavan 2006, *Proc Natl Acad Sci USA*, 103, 7130-7135). For each compound, 3 mice were used and treatment was done by subcutaneous (sc) or intraperitoneal (ip) injection at 10 mpk/day for 4 days for this analysis. The brain-to-plasma ratio (PK) of tropisetron and sAPPalpha/Aβ42 ratios (PD) were then determined.

X-ray scattering data collection: To 100 µg of purified MBP-eAPP$_{230-624}$ were incubated with 50 µM Disulfuram or 50 µM Sulfiram in 20 mM sodium phosphate pH 7.4, 137 mM sodium chloride, 0.05% dimethyl sulfoxide at 4° C. for 1 hour. The control sample was incubated in the buffer alone. The samples were then concentrated to approximately 1.5 mg/ml using 5000-kDa NML concentrators. Small-angle X-ray scattering data were collected using protein concentrations in the range of 0.25-1.5 mg/ml and an X-ray wavelength of 1.11 Å at beam line 12.3.1 (Advanced Light Source). Samples of the filtrate were used for buffer subtraction. Data were integrated with software customized for the beam line and processed with the program PRIMUS (Konarev (2003) *Journal of Applied Crystallography* 36, 1277-1282). The program GNOM (Svergun, (1992) *J. Appl. Crystallogr.* 25, 495-503) was used to calculate the maximum dimension and the radius of gyration and to estimate the intensity of the scattering at zero angle for higher concentration samples. The molecule weight of each protein was calculated by comparing to the scattering of proteins of known molecule weight. The dimensional data for each sample are summarized in Table 4. Although dilutions of each sample were analyzed to concentrations of approximately 0.25 mg/ml, no significant differences were observed in the dimensional data across the concentration ranges shown in Table 4.

TABLE 4

| | | $D_{max}$ (Å) ± 10 | $R_g$ (Å) ± 2 | $MW_{calc}/MW_{seq}$ ± 0.2 |
|---|---|---|---|---|
| MBP-eAPP$_{230-624}$ | -na- | 190 | 55 | 2.0 |
| | Sulfiram | 170 | 53 | 1.7 |
| | Disulfiram | 160 | 51 | 1.5 |

Figure 3:
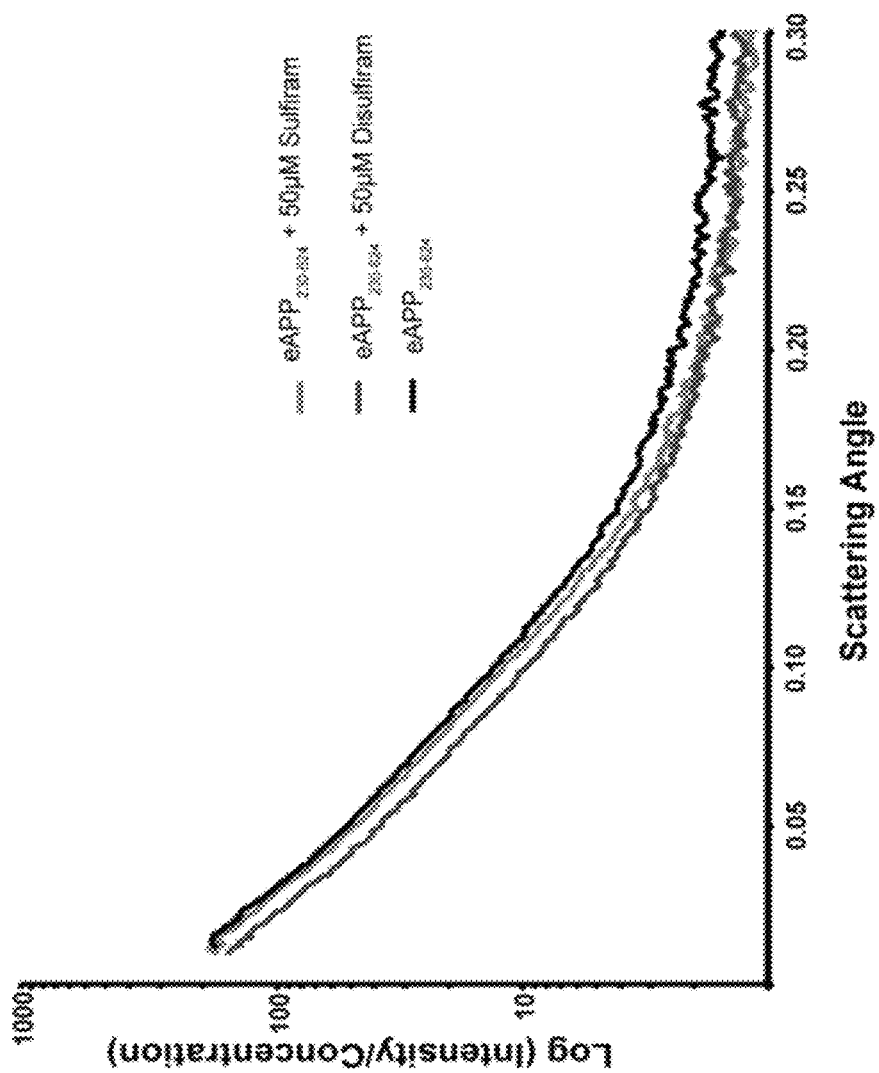
FIG. 3 illustrates an X-ray scattering analysis of eAPP$_{230-264}$ in the presence of sulfuram or disulfuram.
Figure 4:
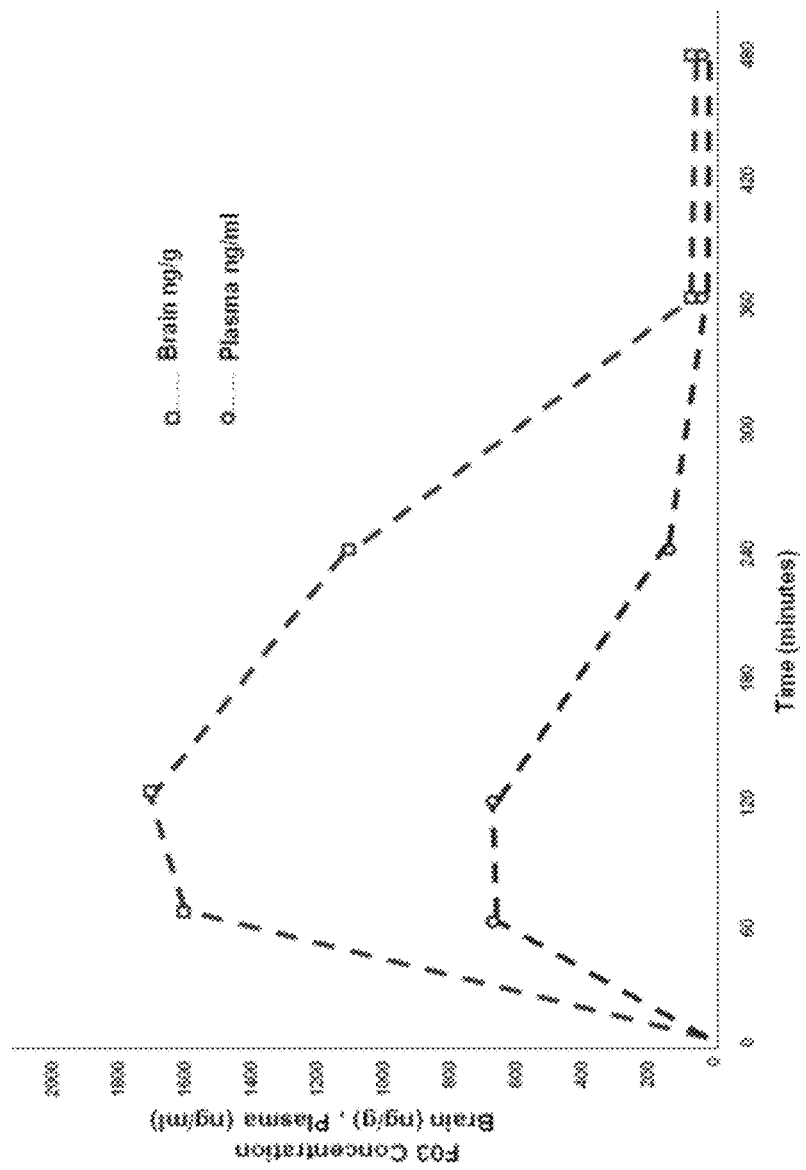
FIG. 4 illustrates a pharmacokinetic analysis of brain and plasma levels of tropisetron hydrochloride (identified as Navoban, F03) in mice after subcutaneous (sc) treatment.
Figure 5:
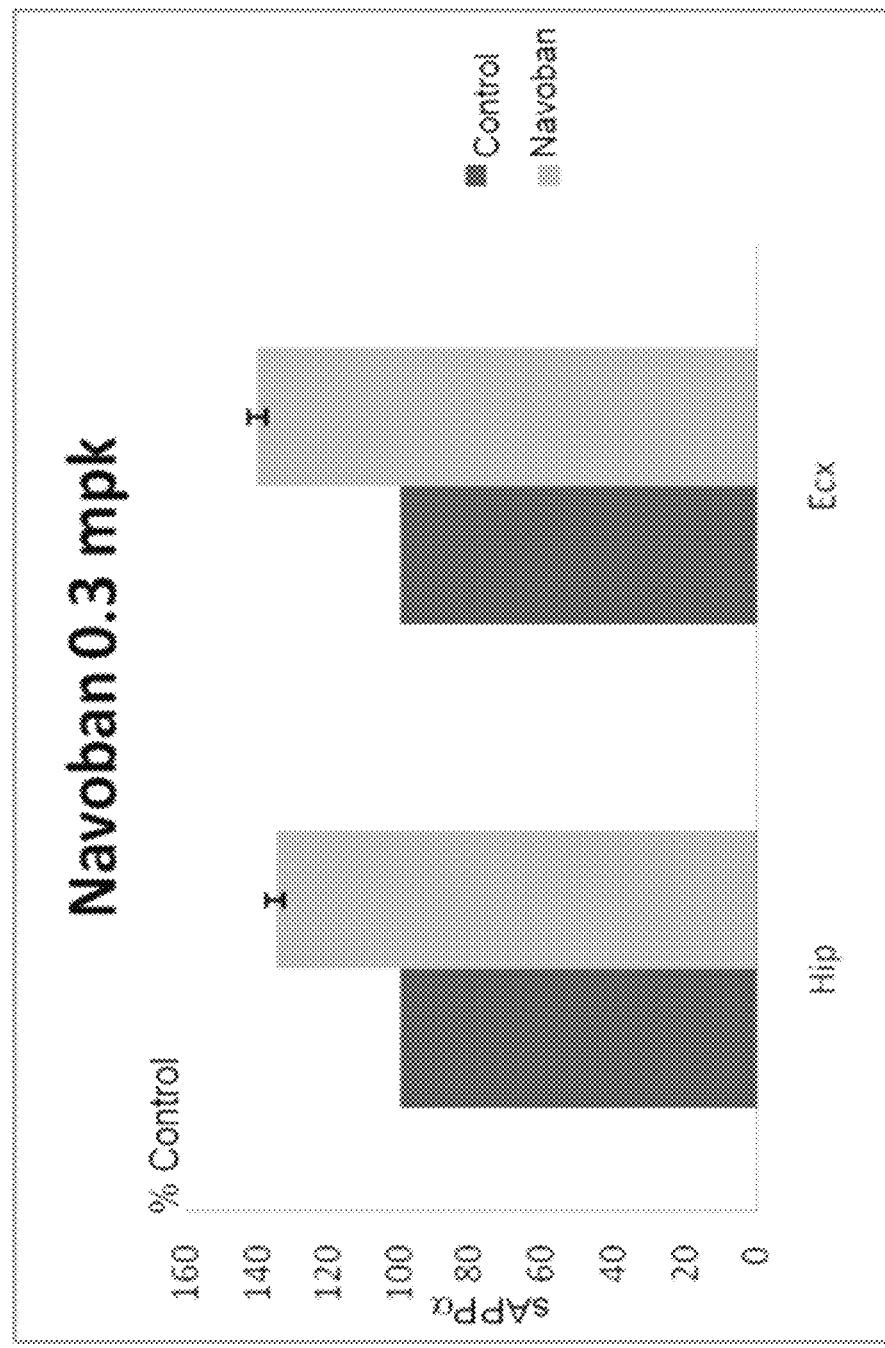
FIG. 5 illustrates that treatment of mice in the AD mouse model with 0.3 mg/kg (mpk) tropisetron hydrochloride (identified as Navoban) for 5 days results in an increase in sAPPα levels in the hippocampus (Hip) and entorhinal cortex (ECx).
Figure 6:
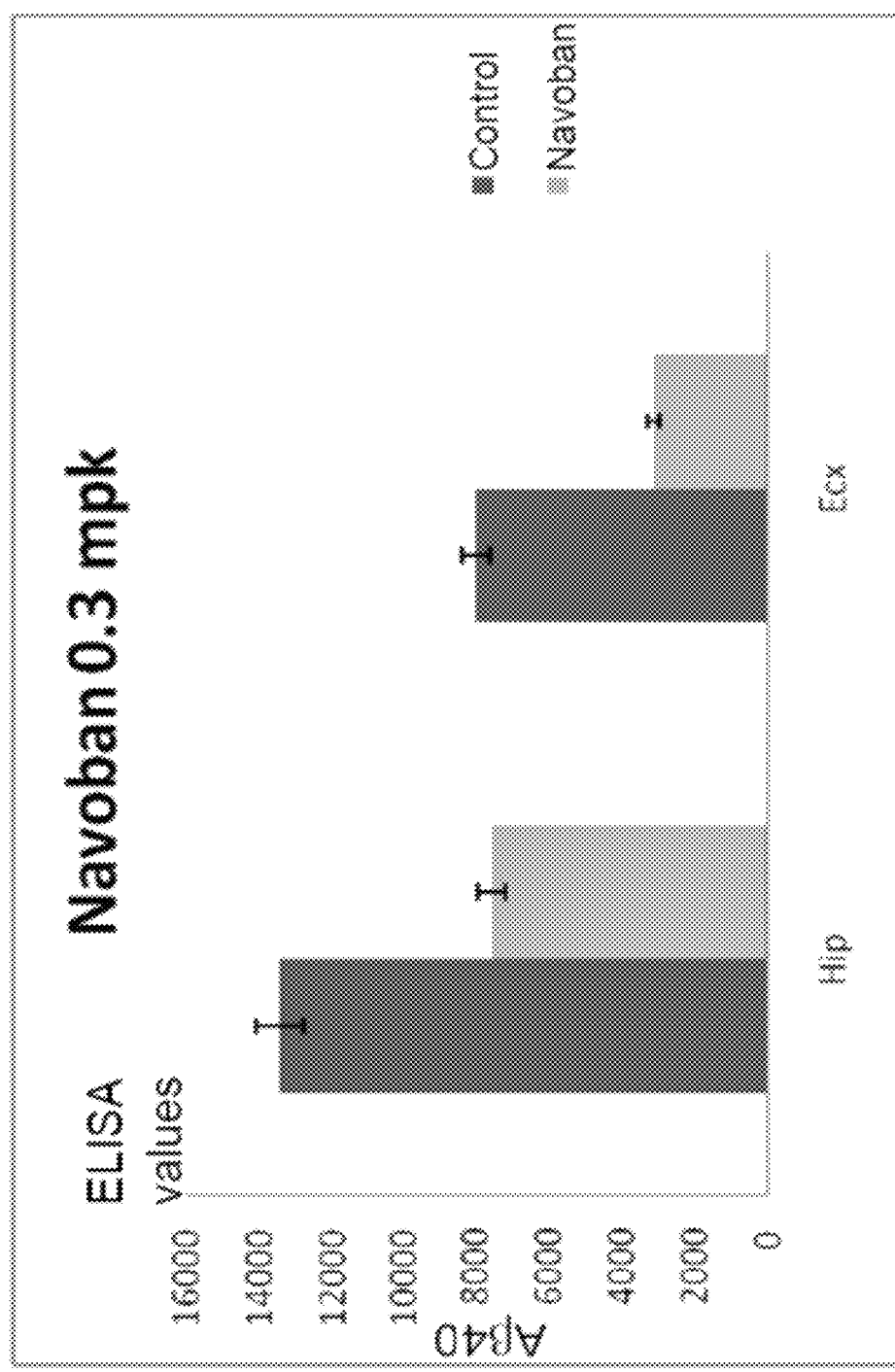
FIG. 6 illustrates that treatment of mice in the AD mouse model with 0.3 mg/kg (mpk) tropisetron hydrochloride (identified as Navoban) for 5 days results in a decrease in Aβ40 levels in the hippocampus (Hip) and entorhinal cortex (ECx).
Figure 7:
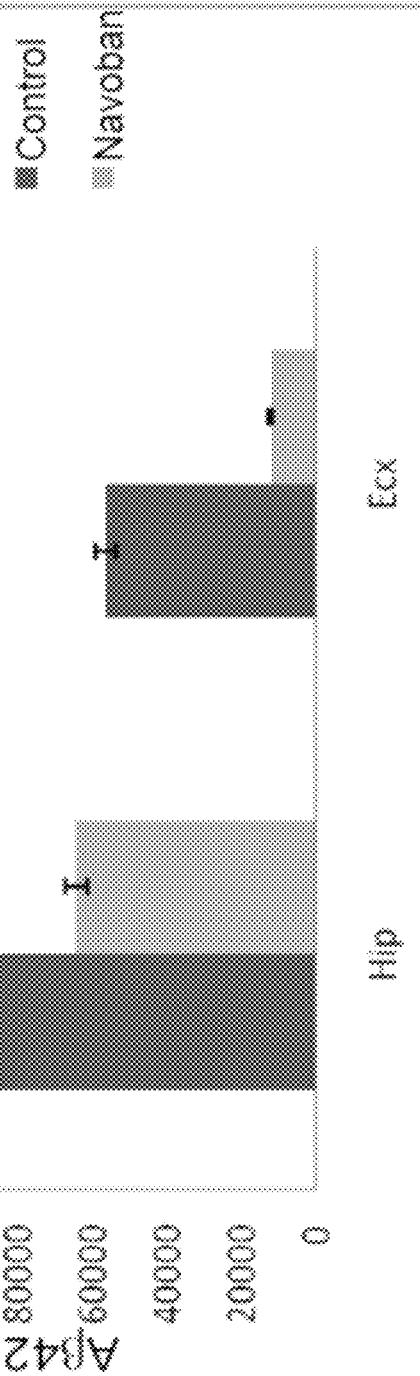
FIG. 7 illustrates that treatment of mice in the AD mouse model with 0.3 mg/kg (mpk) tropisetron hydrochloride (identified as Navoban) for 5 days results in a decrease in Aβ42 levels in the hippocampus (Hip) and entorhinal cortex (ECx).

As shown in FIG. 3, incubation with both disulfuram and sulfuram produced significant changes in the small-angle x-ray scattering of MBP-eAPP$_{230-624}$ indicating that both molecules bind to MBP-eAPP$_{230-624}$ and alter the conformation of the protein. The apparent drop in molecular weight and maximum dimension (Dmax) are consistent with both sulfuram and disulfuram disrupting the MBP-eAPP$_{230-624}$ dimers. The greater effect of disulfuram than sulfuram suggests that disulfuram has a higher binding affinity.

Results

Tropisetron Hydrochloride: The brain uptake testing in mice demonstrated that the tropisetron hydrochloride penetrates the blood-brain-barrier well, with a brain/plasma ratio of about 3 at peak drug levels. Testing in the APP transgenic (Tg) mice at 0.3 milligrams per kilogram (mpk) by the subcutaneous (sc) route over a 5 day period results in significant increase in sAPPa levels in the mouse hippocampal (Hip) and entorhinal cortex (ECx) and a significant decrease in both Aβ40 and Aβ42 levels. This dose of tropisetron is approximately equivalent to the human dose of 5 milligrams per day for a normal adult. The results are shown in FIGS. 4-7.

Figure 8:
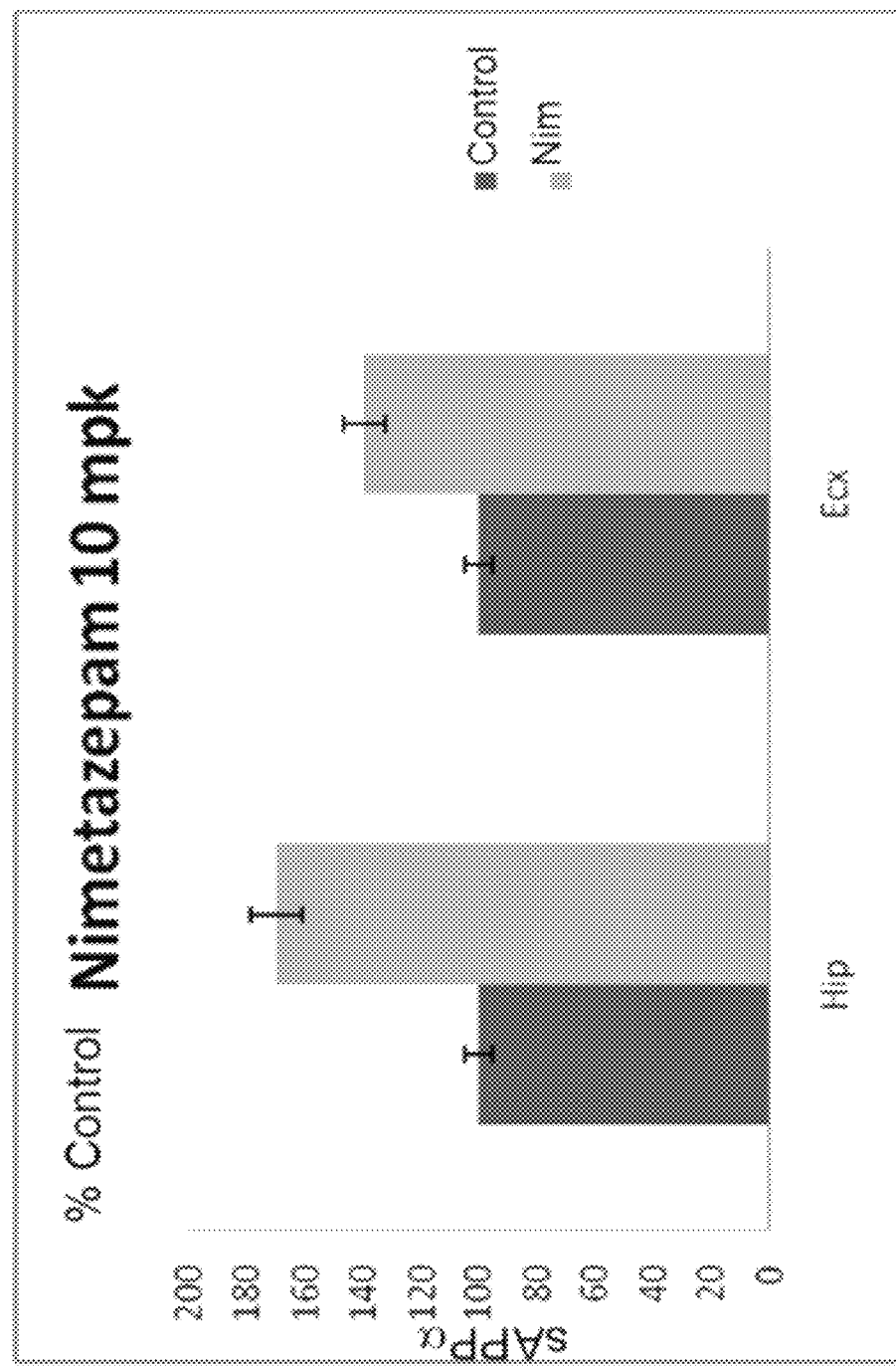
FIG. 8 illustrates that treatment of mice in the AD mouse model with 10 mg/kg (mpk) nimetazepam (Nim) for 5 days results in an increase in sAPPα levels in the hippocampus (Hip) and entorhinal cortex (ECx).

Nimetazepam: Nitmetazepam is a benzodiazepine and is known to cross the blood-brain-barrier well. Testing in the transgenic (Tg) mice at 10 mpk by the subcutaneous (sc) route over a 5 day period resulted in significant increase in sAPPα levels in the mouse hippocampal (Hip) and entorhinal cortex (ECx). No significant changes in either Aβ40 or Aβ42 levels were seen in these experiments. See, FIG. 8.

Honokiol: The brain uptake testing with honokiol shows that the compound penetrates the brain well, with a brain/plasma ratio of about 1. Testing in the transgenic (Tg) mice at 10 mpk by the subcutaneous (sc) route over a 5 day period demonstrated no significant increase in sAPPα levels in the mouse hippocampal (Hip) and entorhinal cortex (ECx). No significant changes in either Aβ40 or Aβ42 levels were seen in these experiments. Chronic testing in Tg mice was not completed.

Disulfiram: The brain uptake testing with Disulfuram demonstrated that it has low blood-brain-barrier penetration, the brain/plasma ratio of less than 0.1. Further testing shows that Disulfuram degrades rapidly in brain tissue, probably being reduced at the disulfide bond. As expected, there were no changes in sAPPα or Aβ levels. Treatment of 7 W cells stably transfected with APP with Disulfuram shows an increase in the sAPPα levels (FIG. 1). Using an X-scattering analysis we have shown that Disulfuram can bind to APP and disrupt APP dimerization (Table 4) and this results in increased a-secretase cleavage of APP and sAPPα levels.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating mild cognitive impairment (MCI) associated with amyloid deposits in the brain in a subject, the method comprising:
   administering tropisetron or a pharmaceutically acceptable salt thereof, to the subject diagnosed as having MCI, where said tropisetron or pharmaceutically acceptable salt thereof is administered in an amount effective to increase in the cerebral spinal fluid (CSF) levels of one or more components selected from the group consisting of sAPPα, sAPPα/sAPPβ ratio, sAPPα/Aβ40 ratio, and sAPPα/Aβ42 ratio.

2. The method of claim 1, wherein said tropisetron is provided as a pharmaceutically acceptable HCl salt.

3. The method of claim 1, wherein the subject is human.

4. The method of claim 1, wherein administration of said tropisetron prevents the progression of MCI to Alzheimer's disease.

5. The method of claim 1, wherein the subject is at risk of developing Alzheimer's disease.

6. The method of claim 5, wherein the subject has a familial risk for having Alzheimer's disease.

7. The method of claim 5, wherein the subject has a familial Alzheimer's disease (FAD) mutation.

8. The method of claim 5, wherein the subject has the APOE ε4 allele.

9. The method of claim 1, wherein the subject is free of and does not have genetic risk factors of Parkinson's disease or schizophrenia.

10. The method of claim 1, wherein the subject is not diagnosed as having or at risk for Parkinson's disease or schizophrenia.

11. The method of claim 1, wherein the subject does not have a neurological disease or disorder other than Alzheimer's disease.

12. The method of claim 1, wherein the subject is not diagnosed as having or at risk for a neurological disease or disorder other than Alzheimer's disease.

13. The method of claim 1, wherein said method provides one or more of the following:
   a reduction of the plaque load in the brain of the subject;
   a reduction in the rate of plaque formation in the brain of the subject;
   an improvement in the cognitive abilities of the subject;
   an improvement in a stabilization of, or a reduction in the rate of decline of the clinical dementia rating (CDR) of the subject; and
   where the subject is a human the mitigation comprises a perceived improvement in quality of life by the human.

14. The method of claim 1, wherein the tropisetron is administered orally.

15. The method of claim 1, wherein the administering is over a period of at least three weeks.

16. The method of claim 1, wherein the administering is over a period of at least 6 months.

17. The method of claim 1, wherein said tropisetron is formulated for administration via a route selected from the group consisting of isophoretic delivery, transdermal delivery, aerosol administration, administration via inhalation, oral administration, intravenous administration, and rectal administration.

18. The method of claim 1, wherein an acetylcholinesterase inhibitor is not administered in conjunction with said tropisetron.

19. The method of claim 18, wherein the acetylcholinesterase inhibitor is selected from the group consisting of tacrine, ipidacrine, galantamine, donepezil, icopezil, zanapezil, rivastigmine, huperzine A, phenserine, physostigmine, neostigmine, pyridostigmine, ambenonium, demarcarium, edrophonium, ladostigil and ungeremine.

20. A method of delaying the onset of MCI, or Alzheimer's disease in an asymptomatic subject, the method comprising:
   administering to said asymptomatic subject an amount of tropisetron, or its pharmaceutically acceptable salt, effective to increase in the cerebral spinal fluid (CSF) levels of one or more components selected from the group consisting of sAPPα, sAPPα/sAPPβ ratio, sAPPα/Aβ40 ratio, and sAPPα/Aβ42 ratio.

21. The method of claim 20, wherein the subject is at risk of developing mild cognitive impairment (MCI) associated with amyloid deposits in the brain, or Alzheimer's disease.

22. The method of claim 20, wherein the subject is a human and progression from an asymptomatic state to a symptomatic state of MCI is delayed.

23. The method of claim 20, wherein said tropisetron is administered orally.

24. The method of claim 20, wherein the administering is over a period of at least three weeks.

* * * * *